US006890994B2

(12) United States Patent
Ohrbom et al.

(10) Patent No.: US 6,890,994 B2
(45) Date of Patent: May 10, 2005

(54) CURABLE COATING COMPOSITIONS WITH CARBAMATE-CONTAINING ACRYLIC POLYMERS

(75) Inventors: Walter H. Ohrbom, Hartland Township, MI (US); Craig S. Schang, Brighton, MI (US); Donald Campbell, Hartland, MI (US); Donald L. St. Aubin, Commerce Township, MI (US)

(73) Assignee: BASF Corporation, Southfield, MI (US)

( * ) Notice: Subject to any disclaimer, the term of this patent is extended or adjusted under 35 U.S.C. 154(b) by 108 days.

(21) Appl. No.: 10/305,284

(22) Filed: Nov. 26, 2002

(65) Prior Publication Data

US 2004/0087747 A1 May 6, 2004

Related U.S. Application Data

(63) Continuation-in-part of application No. 10/285,634, filed on Oct. 31, 2002, and application No. 10/285,600, filed on Oct. 31, 2002, and application No. 10/285,594, filed on Oct. 31, 2002.

(51) Int. Cl.$^7$ ................................................ C08F 2/00
(52) U.S. Cl. ...................... 525/242; 525/162; 525/452; 525/481; 428/418; 428/447
(58) Field of Search ................................ 525/242, 481, 525/162, 452, 518; 428/418, 447

(56) References Cited

U.S. PATENT DOCUMENTS

| | | | |
|---|---|---|---|
| 2,979,514 A | 4/1961 | O'Brien | 260/340.2 |
| 4,301,257 A | 11/1981 | Zengel et al. | 525/329 |
| 4,710,542 A | 12/1987 | Forgione et al. | 525/127 |
| 4,758,632 A | 7/1988 | Parekh et al. | 525/383 |
| 4,939,213 A | 7/1990 | Jacobs, III et al. | 525/329.9 |
| 5,084,541 A | 1/1992 | Jacobs, III et al. | 528/45 |
| 5,288,865 A | 2/1994 | Gupta | 544/200 |
| 5,356,669 A | 10/1994 | Rehfuss et al. | 427/407.1 |
| 5,373,069 A | 12/1994 | Rehfuss et al. | 525/456 |
| 5,474,811 A | 12/1995 | Rehfuss et al. | 427/407.1 |
| 5,512,639 A | 4/1996 | Rehfuss et al. | 525/456 |
| 5,552,497 A | 9/1996 | Taylor et al. | 525/456 |
| 5,605,965 A | 2/1997 | Rehfuss et al. | 525/100 |
| 5,719,237 A * | 2/1998 | Rehfuss et al. | 525/419 |
| 5,907,024 A * | 5/1999 | Ohrbom et al. | 528/75 |
| 5,945,499 A | 8/1999 | Ohrbom et al. | 528/75 |
| 5,964,928 A | 10/1999 | Tomlinson | 106/14.21 |
| 5,994,479 A * | 11/1999 | Green et al. | 525/481 |
| 6,262,297 B1 | 7/2001 | Clements et al. | 560/157 |
| 6,303,690 B1 * | 10/2001 | December et al. | 525/163 |
| 6,362,285 B1 | 3/2002 | Ohrbom et al. | 525/330.5 |
| 6,376,607 B1 * | 4/2002 | Ambrose et al. | 525/101 |
| 6,391,968 B1 * | 5/2002 | Ohrbom et al. | 525/162 |
| 6,580,001 B1 | 6/2003 | Bowman et al. | 558/260 |
| 2002/0123545 A1 | 9/2002 | Yajking et al. | 524/196 |
| 2002/0147279 A1 * | 10/2002 | Ohrbom et al. | 525/157 |
| 2003/0100682 A1 * | 5/2003 | Ohrbom et al. | 525/242 |
| 2003/0165588 A1 * | 9/2003 | Desai et al. | 428/418 |

FOREIGN PATENT DOCUMENTS

| | | | |
|---|---|---|---|
| DE | 1063146 | 7/1958 | |
| DE | 1593331 | 10/1966 | |
| DE | 44 32 897 | 3/1996 | C08L/61/20 |
| EP | 245 700 | 4/1987 | C07D/251/54 |
| EP | 594 068 | 10/1993 | C09D/201/02 |
| EP | 594 071 | 10/1993 | C09D/201/02 |
| EP | 594 142 | 10/1993 | C08L/57/12 |
| EP | 604 922 | 12/1993 | C08K/5/3492 |
| EP | 850 986 | 12/1997 | C08K/5/3492 |
| GB | 843331 | 8/1957 | |
| GB | 1068650 | 12/1965 | C07C/125/04 |
| WO | WO94/10211 | 5/1994 | C08F/8/30 |
| WO | WO94/10212 | 5/1994 | C08F/8/30 |
| WO | WO94/10213 | 5/1994 | C08F/8/30 |
| WO | WO 01/56978 | 8/2001 | C08K/5/205 |

OTHER PUBLICATIONS

Ohrbom, et al. U.S. Appl. No. 10/285,634, entitled Compounds having a secondary or tertiary hydroxyl or halide group separated from a primary carbamate group by three or more carbon atoms and a method of making the same, pp. 1–31 and abstract,.

Ohrbom, et al. U.S. Appl. No. 10/285,600 entitled Curable coating compositions containing reactive compounds having a secondary or tertiary hydroxy or halide group separated from a primary carbamate geoup by three or more carbon atoms, pp. 140 and abstract,.

Ohrbom, et al. U.S. Appl. No. 10/10/285,594 entitled Carbamate functional ,materials, a method of making said material, and curable coating compositions containing said materials, pp. 1–49 and abstract,.

(Continued)

Primary Examiner—David W. Wu
Assistant Examiner—Henry S. Hu

(57) ABSTRACT

The invention provides an acrylic polymer or oligomer comprising random repeating units of the formula:

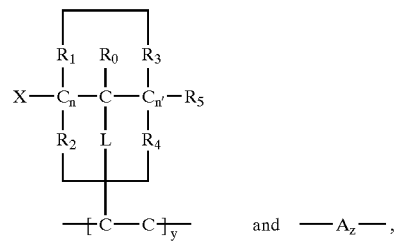

a method of making said polymers and curable coating compositions comprising the same.

58 Claims, No Drawings

OTHER PUBLICATIONS

Database CA, online!, Chemical Abstract Service, Database Accession No. 128:2060676 CA, 1998, XP002265958.

English Abstract for JP 05138614, entitled "Persistent Preservative for Timber" Michihiko, et al., Date of Publication Jun. 8, 1993.

English Abstract for JP 2002242075, entitled "Mildewproof base fabric for night cover for refrigerator–freezer", date of publication Aug. 28, 2002.

English Abstract for JP 63301251, entitled " Coating composition" Shuichi, et al., date of Publicaiton Dec. 8, 1988.

English Abstract for JP 05229973, entitled "Comprises adol condensation–dehydration of PrCHO in presence of aq. Alk. Soln. Catalyst, removal", et al., Date of Publication Sep. 7, 1993.

Leon Palfray, et al., Compt. Rend. (1941) vol. 212, pp. 911 to 913 AN 1943:29287 Caplus.

BASF Coating AG, U.S. Appl. No. 10/182,528, filed Jul. 22, 2002, pp. 1–40.

Marvin L. Green, et al., entitled "Low VOC carbamate functional coatings compositions for automotive topcoats", Mar. 1–3, 2000, New Orleans, LA, USA.

W. Albert Noves, Jr.The Journal of the American Chemical Society, vol. LXXIII, 1951.

Shalom Sarel, et al. Organic Carbonates IV, entitled Factors Affecting Formation of Carbonates Homologous Cyclic, pp. 1873–1878, Dec. 1959.

J. Med. Chem., B. J. Ludwig, et al., entitled Carbamata derivatives related to ,meprobamate, vol. 12, 1969, pp. 462–472.

* cited by examiner

CURABLE COATING COMPOSITIONS WITH CARBAMATE-CONTAINING ACRYLIC POLYMERS

This application is a continuation in part of Ser. Nos. 10/285,600, 10/285,594, and 10/285,634, all filed Oct. 31, 2002, all of which are hereby incorporated by reference.

BACKGROUND OF THE INVENTION

Curable coating compositions such as thermoset coatings are widely used in the coatings art. They are often used for topcoats in the automotive and industrial coatings industry.

High-gloss and color-plus-clear composite coatings are particularly useful as topcoats where exceptional gloss, depth of color, distinctness of image, or special metallic effects are desired. The automotive industry has made extensive use of these coatings for automotive body panels. These coatings require an extremely high degree of clarity and a low degree of visual aberrations at the surface of the coating in order to achieve desired visual effects such as a high distinctness of image (DOI).

As a result, high-gloss and composite color-plus-clear coatings are susceptible to a phenomenon known as environmental etch. Environmental etch manifests itself as spots or marks on or in the finish of the coating that often cannot be rubbed out. It is often difficult to predict the degree of resistance to environmental etch that a high gloss or color-plus-clear composite coating will exhibit. Many coating compositions known for their durability and/or weatherability when used in exterior paints, such as high-solids enamels, do not provide the desired level of resistance to environmental etch when used in high gloss coatings and color-plus-clear composite coatings.

Many compositions have been proposed for use as the clearcoat of a color-plus-clear composite coating, such as polyurethanes, acid-epoxy systems and the like. However, many prior art systems suffer from disadvantages such as coatability problems, compatibility problems with the pigmented basecoat, solubility problems. Moreover, very few one-pack coating compositions have been found that provide satisfactory resistance to environmental etch, especially in the demanding environment of automotive coatings.

It has been found that carbamate functional polymers such as those described in U.S. Pat. No. 5,356,669 can be used to provide coating compositions which exhibit significantly improved environmental etch resistance. Carbamate functional polymers have been used to provide commercially advantageous coatings compositions, especially as clearcoats in composite color-plus-clear coatings.

Unfortunately, some carbamate functional compounds and/or polymers known in the prior art are vulnerable to instability and decomposition, especially with respect to the formation of cyclic carbonates and carbamates. This results in difficulties in manufacturing and storage.

It has also been difficult to make thermally stable hydroxy functional mono-carbamate functional compounds in an efficient and cost effective manner. In particular, what is desired is a commercially feasible method of making such compounds that utilizes cost effective starting compounds such as polyols and diols.

In addition, although coating compositions containing carbamate functional polymers generally provide the performance properties currently required by the automotive industry, continuous improvement is always desired. As a result, it would be advantageous to provide improvements in solids or % nonvolatile, flexibility, scratch & mar resistance, cold crack resistance, chip resistance and/or the like. At the same time, such improvements must be achieved without any decrease in environmental etch resistance or other commercially required performance property.

It would also be desirable to provide such a technology which would be applicable for use in a wide variety of coating compositions and applications, such as primers, basecoats, clearcoats, two-component systems, anti-chip coating compositions, water borne coatings, solvent borne coatings, coatings for flexible substrates, powder coatings, solventless powder-slurry coatings, solventless liquid coatings, and the like.

Finally, it would be advantageous to provide improved etch resistant coating compositions which have an increased % NV (nonvolatile) or decreased VOC (volatile organic content) at a sprayable viscosity.

The prior art has failed to address and rectify these issues.

The preparation of monocarbamate alcohols by the ammonolysis of cyclic carbonates prepared from substituted propanediols is disclosed in *Some Anticonvulsant Agents Derived from 1,3-Propanediols*, Ludwig, B. J. and Piech, E. C.; J. Am Chem. Soc. (1951) 73 5779–81. CAN 47:3228.

U.S. Pat. No. 5,719,237, Rehfuss et al., discloses the use of carbamate functional compounds (a) having a plurality of carbamate groups prepared by a transcarbamylation reaction wherein an alcohol or hydroxylalkyl carbamate is reacted with an alkyl carbamate. The '237 patent teaches that it is desirable to avoid the inclusion of hydroxyl groups in compound (a) as such hydroxyl groups lead to the formation of vulnerable ether bridges.

U.S. Pat. No. 5,907,024, Ohrbom et al., and U.S. Pat. No. 5,945,499 disclose the use of hydroxyalkyl carbamates of the general structure

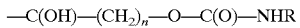

—C(OH)—(CH$_2$)$_n$—O—C(O)—NHR wherein n is an integer from 0 to 6 and R is H or an alkyl group of from 1 to 4 carbons.

U.S. Pat. No. 5,760,127, Bammel et al, and U.S. Pat. No. 6,262,297, Clements et al., disclose hydroxyalkylcarbamate compositions produced by the reaction of anhydrous ammonia or aqueous ammonium hydroxide with a six-membered cyclic carbonate. Bammel et al discloses that five-membered rings are preferred, not as a result of better performance, but as a result of their ease of synthesis and greater degree of commercial availability. Clements et al teaches that six-membered rings are preferred due to increased stability. However, the cost and commercial availability of the six-membered cyclic carbonates renders the process and resultant products to be less than cost effective. Also, depending on the location of any substituent groups on the starting cyclic carbonate, the process disclosed in Clements produces a reaction product which is a compound comprising a mixture of structures with varying reactivity and selectivity.

WO 0156978, Rink, et al discloses positionally isomeric diethyloctanediol dicarbamates and diethyloctanediols diallophanates. The dicarbamate and diallophanate species have no hydroxyl functionality and are made from position isomers of diethyloctane diols.

Despite these and other attempts by the prior art, the prior art has failed to provide a cost effective and efficient manner of making hydroxy functional mono-carbamate functional compounds from polyols and diols. Moreover, the prior art has particularly failed to provide such hydroxy functional mono-carbamate functional compounds that possess improved stability with respect to decomposition and the formation of undesirable cyclic carbonates and carbamates. As a result, the prior art has failed to provide carbamate functional acrylic polymers and/or oligomers that utilize such hydroxy functional mono-carbamate functional compounds as reactants and thus obtain the benefits thereof.

Accordingly, it is an object of the invention to provide carbamate functional acrylic polymers and/or oligomers which are made with compounds that possess improved stability with respect to the decomposition and the formation of undesirable cyclic carbonates and carbamates.

It is an another object of the invention to provide primary carbamate functional acrylic polymers and oligomers which are made from the polymerization reaction of primary carbamate functional ethylenically unsaturated monomers made from the reaction of mono-carbamate functional compounds containing hydroxy groups, halide groups or derivatives thereof with ethylenically unsaturated monomers containing one or more groups reactive with hydroxy groups, halide groups, or derivatives thereof.

It is a further object of the invention to provide curable coating compositions containing carbamate functional materials which provide all of the advantages of prior art carbamate containing coating compositions, especially good environmental etch resistance, but further exhibit increased % NV (nonvolatile) or decreased VOC (volatile organic content) at a sprayable viscosity, and a desirable applied appearance.

It is also an object of the invention to provide curable coating compositions which provide all of the advantages of prior art carbamate containing coating compositions, especially good environmental etch resistance, but further exhibit improvement in one or more finished film performance parameters such as flexibility, scratch and mar resistance, and/or chip resistance.

It is another object of the invention to provide a technology for improving one or more of the following performance parameters, i.e., % nonvolatile solids, flexibility, scratch and mar resistance, and/or chip resistance, in a wide variety of coating compositions and applications, such as primers, basecoats, clearcoats, two-component systems, anti-chip coating compositions, water borne coatings, solvent borne coatings, coatings for flexible substrates, solventless coatings, powder coatings, and the like.

SUMMARY OF THE INVENTION

These and other objects of the invention have been met with the use of a specific primary carbamate functional ethylenically unsaturated monomer. The primary carbamate functional ethylenically unsaturated monomer of the invention must be of the structure:

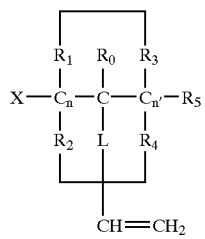

wherein X is a primary carbamate group, n is an integer of 2 or more, n' is an integer of 1 or more, $R_0$, $R_1$, $R_2$, $R_3$, $R_4$ and $R_5$ are independently H, an alkyl group, an aromatic group, or mixtures thereof, at least one $R_1$ or $R_2$ group is not hydrogen, and L is a linking group.

The primary carbamate functional ethylenically unsaturated monomer of the invention comprises the reaction product of (1) an ethylenically saturated monomer comprising one or more functional groups (i) which are reactive with a functional group Z but which are substantially nonreactive with a primary carbamate group X of monomeric reactive compound (2), and (2) a monomeric reactive compound comprising one or more structures of the formula:

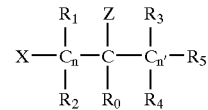

wherein X is a primary carbamate group, Z is a functional group reactive with at least one functional group of material (1) and is selected from the group consisting of hydroxy groups, halide groups, and derivatives thereof, n is an integer of 2 or more, n' is an integer of 1 or more, and $R_0$, $R_1$, $R_2$, $R_3$, $R_4$ and $R_5$ are independently H, an alkyl group, an aromatic group, or mixtures thereof, with the provisos that (i) at least one $R_1$ or $R_2$ group is not hydrogen, and (ii) in substantially all structures of monomeric reactive compound (2), primary carbamate group X is attached to a carbon atom having a lower degree of substitution than a carbon atom to which functional group Z is attached.

The primary carbamate functional acrylic polymer of the invention comprises randomly repeating units of the formula:

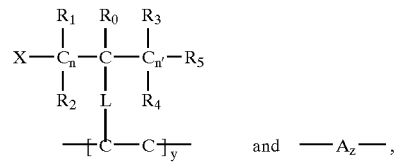

wherein X is a primary carbamate group, n is an integer of 2 or more, n' is an integer of 1 or more, $R_0$, $R_1$, $R_2$, $R_3$, $R_4$ and $R_5$ are independently H, an alkyl group, an aromatic group, or mixtures thereof, at least one $R_1$ or $R_2$ group is not hydrogen, L is a linking group, y represents from 2 to 100% by weight, based on the total weight of all ethylenically unsaturated monomers in the monomer mixture, A represents functional or nonfunctional repeating units derived from one or more other ethylenically unsaturated monomers, z represents from 0% to 98% by weight, based on the total weight of all ethylenically unsaturated monomers in the monomer mixture, but with the proviso that substantially all primary carbamate groups X are attached to carbon atoms having a lower degree of substitution than a carbon atom to which linking group L is attached. The primary carbamate functional acrylic polymer of the invention is the polymerization reaction product of a monomer mixture comprising the primary carbamate functional ethylenically unsaturated monomer of the Invention.

DETAILED DESCRIPTION OF THE PREFERRED EMBODIMENTS

The instant invention provides a primary carbamate functional acrylic polymer comprising randomly repeating units of the formula:

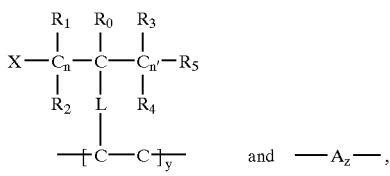

and  —A$_z$—, wherein x is a primary carbamate group, n is an integer of 2 or more, n' is an integer of 1 or more, $R_0$, $R_1$, $R_2$, $R_3$, $R_4$ and $R_5$ are independently H, an alkyl group, an aromatic group, or mixtures thereof, at least one $R_1$ or $R_2$ group is not hydrogen, L is a linking group, y represents from 2 to 100% by weight, based on the total weight of all ethylenically unsaturated monomers in the monomer mixture, A represents nonfunctional or functional repeating units derived from one or more other ethylenically unsaturated monomers, z represents from 0% to 98% by weight, based on the total weight of all ethylenically unsaturated monomers in the monomer mixture, but with the proviso that substantially all primary carbamate groups X are attached to carbon atoms having a lower degree of substitution than a carbon atom to which linking group L is attached.

The primary carbamate functional acrylic polymer of the invention results from the polymerization of a monomer mixture comprising a primary carbamate functional ethylenically unsaturated monomer of the structure:

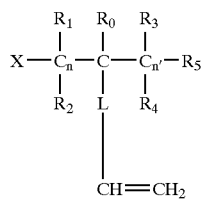

wherein X is a primary carbamate group, n is an integer of 2 or more, n' is an integer of 1 or more, $R_0$, $R_1$, $R_2$, $R_3$, $R_4$ and $R_5$ are independently H, an alkyl group, art aromatic group, or mixtures thereof, at least one $R_1$ or $R_2$ group is not hydrogen, and L Is a linking group.

In the ethylenically unsaturated monomer of the invention, X is a primary carbamate group. As used herein, "primary carbamate group" refers to the functional group having the structure

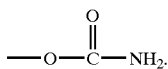

Thus, the primary carbamate groups of the ethnically unsaturated monomer and the acrylic polymer of the invention may be defined as a terminal or pendent carbamate groups.

In general, $R_0$, $R_1$, $R_2$, $R_3$, $R_4$ and $R_5$ may be H or an alkyl group, an aromatic group, or mixtures thereof. Illustrative alkyl groups are aliphatic groups and cycloaliphatic groups. Suitable alkyl and aromatic containing groups will generally have from one to sixteen carbon atoms and may be linear or branched. As used herein, the term "branched" refers to both lateral branches and forked branches. Lateral refers to a branch of two small chains at the end atom of a carbon chain. Forked refers to a branch of two small chains in the middle of a carbon chain. Any individual substituent may have both branching and forking therein. In addition, it is within the scope of the invention for two or more of the various R substituents to be connected with each other. As noted above $R_0$ may be H or an alkyl or aromatic group containing substituent.

In a most preferred embodiment $R_0$ will be H so that the linking group L is a secondary functional group. If $R_0$ is not hydrogen, suitable groups are those groups selected from the group of aliphatic groups, cycloaliphatic groups, aromatic groups and mixtures thereof. Preferred for use as $R_0$ are aliphatic and cycloaliphatic groups, with aliphatic groups being most preferred for use as $R_0$. Particularly suitable groups for use as $R_0$ are aliphatic groups and cycloaliphatic groups containing from one to sixteen carbon atoms, with aliphatic groups containing one to twelve carbon atoms being preferred if $R_0$ is an alkyl group and aliphatic groups containing one to eight carbon atoms being most preferred if $R_0$ is an alkyl group. Finally, it is within the scope of the invention that $R_0$ be an alkyl or aromatic group connected to any of the other $R_{1-5}$ substituents.

$R_1$, $R_2$, $R_3$, $R_4$ and $R_5$ may be H or a group as defined above for $R_0$.

However, it is an aspect of the invention that at least one $R_1$ or $R_2$ group must be selected from the group consisting of aliphatic groups, cycloaliphatic groups, aromatic groups, and mixtures thereof. That is, at least one of the $R_1$ and $R_2$ substituent groups must be other than hydrogen so long as primary carbamate group X is attached to a carbon atom having a lower degree of substitution than the carbon atom to which linking group L is attached. Illustrative groups suitable for use as the $R_1$ or $R_2$ group that is not hydrogen are as defined above for $R_0$. Preferred for use as $R_1$ and $R_2$ are aliphatic and cycloaliphatic groups, with aliphatic groups being most preferred for use as $R_1$ or $R_2$ if they are not hydrogen Particularly suitable non-hydrogen groups for use as $R_1$ and $R_2$ are aliphatic groups and cycloaliphatic groups containing from one to sixteen carbon atoms, with aliphatic groups containing from one to twelve carbon atoms being preferred if $R_1$ or $R_2$ is an alkyl group and aliphatic groups containing one to eight carbon atoms being most preferred if $R_1$ or $R_2$ is an alkyl group. Finally, it is within the scope of the invention that $R_1$ or $R_2$ be an alkyl or aromatic group connected to any of the other $R_{0, 3-5}$ substituents.

As noted above, because primary carbamate group X must be attached to a carbon atom having a lower degree of substitution than the carbon atom to which linking group L is attached, at least one of the substituents $R_1$ and $R_2$ must be hydrogen for the carbon to which X is attached. This requirement is consistent with the requirement that at least one $R_1$ or $R_2$ group must be selected from the group consisting of aliphatic groups, cycloaliphatic groups, aromatic groups and mixtures thereof. When n is 2 and $R_0$ is not hydrogen, the at least one $R_1$ or $R_2$ group that is not hydrogen may be a substituent of the carbon immediately adjacent to the carbon attached to the primary carbamate group X. That is, the carbon to which the carbamate group is attached may have a primary or secondary degree of substitution. When n is greater than 2 and $R_0$ is not hydrogen, the at least one $R_1$ or $R_2$ group that is not hydrogen may be a substituent of the carbon to which the carbamate group is attached or to any of the carbons between the carbon attached to the primary carbamate group X and the carbon attached to the linking group L, i.e., the $C_n$ carbons.

However, it is preferred that the at least one $R_1$ or $R_2$ group which is not hydrogen be attached to a carbon not directly attached to the carbamate group X. More preferably, the at least one $R_1$ or $R_2$ group that is not hydrogen will preferably be attached to a carbon atom located in closer proximity to linking group L rather than functional X. When n is two, it will be appreciated that the at least one $R_1$ or $R_2$ group which is not hydrogen will most preferably be attached to a carbon atom located an equal distance between the carbons to which the functional group X and the linking group L are attached. When n is three or greater, the at least one $R_1$ or $R_2$ group which is not hydrogen will most preferably be attached to the carbon atom which is adjacent to the carbon atom to which the linking group L is attached or be in closer proximity thereto than to the carbon atom to which functional group X is attached.

It is another aspect of the invention that n be an integer of 2 or more so that functional group X and linking group L are separated by at least three carbon atoms, including the carbon atoms to which are attached the functional group X and the linking group L. In one preferred embodiment of the invention, n will be an integer of from 2 to 12, more preferably from 2 to 8, and most preferably from 2 to 4. In another embodiment of the invention, n will be an integer of at least 3, more preferably from 3 to 12, and most preferably from 3 to 4.

In the primary carbamate functional ethylenically unsaturated monomer used herein, n' must be an integer of 1 or more and may not be 0. In a preferred embodiment of the invention, n' will be an integer of from 1 to 16, more preferably from 1 to 12, and most preferably n' will be an integer of from 1 to 8.

As noted above, $R_3$, $R_4$ and $R_5$ are selected from the group consisting of H, $C_1$–$C_{16}$ aliphatic groups, cycloaliphatic groups, aromatic groups, and mixtures thereof. In a preferred embodiment of the invention, $R_3$, $R_4$ and $R_5$ may be selected from the group consisting of H, aliphatic groups, cycloaliphatic groups, and mixtures thereof. In a most preferred embodiment, $R_3$, $R_4$ and $R_5$ will be selected from the group consisting of H, aliphatic groups, and mixtures thereof. In one embodiment according to the invention, $R_3$, $R_4$ and $R_5$ may be connected to $C_{n'}$, $R_0$, $R_1$ or $R_2$ to form a cyclic ring.

It is another aspect of the invention that in general, it is preferred that at least one of $R_3$, $R_4$ and $R_5$ will be a group other than hydrogen when n' is greater than 1. In a preferred embodiment, at least two of $R_3$, $R_4$ and $R_5$ will be other than hydrogen, i.e., $C_1$–$C_{16}$ aliphatic groups, cycloaliphatic groups, aromatic groups, and mixtures thereof, when n' is greater than 1. In a most preferred embodiment of the invention, when n' is greater than one, at least three of $R_3$, $R_4$ and $R_5$ will be selected from the group of $C_1$–$C_{16}$ aliphatic groups, cycloaliphatic groups, aromatic groups, and mixtures thereof.

L is a polyvalent linking group comprising the reaction residue from the reaction between an ethylenically unsaturated monomer (1) and a monomeric reactive compound (2) as discussed below. Illustrative examples of polyvalent linking groups L include esters, ethers, urethanes, ureas, silanes, and the like. Preferred linking groups are urethanes, ureas, and esters with urethanes and esters being most preferred as linking group L.

It will be appreciated that linking group L may comprise functional groups which are pendant to the primary carbamate functional ethylenically unsaturated monomer of the invention. Illustrative functional groups which may be part of linking group L include hydroxy groups, primary carbamate groups, acid groups, silane groups, amide groups, isocyanate groups, epoxy groups, and the like. For example, the primary carbamate functional ethylenically unsaturated monomer of the invention may be the reaction product of a reaction between the monomeric reactive compound (2) and a cyclic anhydride which is then reacted with glycidyl methacrylate. The resulting final monomer has a primary carbamate group X and a pendant hydroxy group within linking group L.

The primary carbamate functional ethylenically unsaturated monomers of the invention can be made in a variety of ways.

For example, the primary carbamate functional ethylenically unsaturated monomers can be made by the reaction of an organometallic acrylate such as sodium methacrylate with a monomeric reactive compound (2) when Z is a halide such as chloride. When Z is a hydroxy group, the primary carbamate functional ethylenically unsaturated monomers of the invention can be made by reaction with an isocyanate functional material such as isocyanate ethyl acrylate, or by reaction with an anhydride such as methacrylic anhydride, or by esterification/transesterification reactions with materials such as acrylic acid or t-butyl acrylate.

In a most preferred embodiment, the primary carbamate functional ethylenically unsaturated monomers of the invention comprise the reaction product of (1) an ethylenically unsaturated monomer comprising one or more functional groups (i) which are reactive with a functional group Z but which are substantially nonreactive with a primary carbamate group X of monomeric reactive compound (2), and a monomeric reactive compound (2).

Monomeric reactive compound (2) comprises one or more structures of the formula:

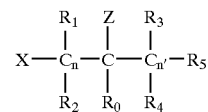

wherein X is a primary carbamate group, Z is a functional group reactive with at least one functional group of material P and is selected from the group consisting of hydroxy groups, halide groups, and derivatives thereof, n is an integer of 2 or more, n' is an integer of 1 or more, and $R_0$, $R_1$, $R_2$, $R_3$, $R_4$ and $R_5$ are independently H, an alkyl group, an aromatic group, or mixtures thereof. In addition, it is a necessary aspect of the invention that (i) at least one $R_1$ or $R_2$ group is not hydrogen, and (ii) in substantially all structures, primary carbamate group X is attached to a carbon atom having a lower degree of substitution than a carbon atom to which functional group Z is attached.

The term structures as used herein refers to Isomers that satisfy the requirements of the instant invention. "Isomers" as used herein refers to structural and position isomers that have the same empirical chemical formula. Structures as used herein refer to those isomers that have the same empirical chemical formula but which satisfy the requirements of the instant formula. For the purposes of the instant invention, it will be appreciated that a single compound may comprise one or more than one structure. Illustrative examples of structural isomers are 2-ethyl-1,3-hexanediol and 2-propyl-1,3-pentanediol. Illustrative examples of position isomers are 2-ethyl-1,3-hexanediol and 2-ethyl-1,4-hexanediol. Illustrative examples of isomers which are both structural and position isomers are 2-ethyl-1,3-hexanediol and 2propyl-1,4-pentanediol. However, it will be appreciated that only those isomers that satisfy the requirements of the instant invention may be structures of the reactive compound of the invention, i.e., they must (1) be of the formula:

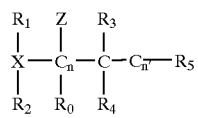

wherein X is a primary carbamate group, Z is either a hydroxy group, a halide group or a derivative thereof, n is as integer of 2 or more, n' is an integer of 1 or more, and $R_0$, $R_1$, $R_2$, $R_3$, $R_4$ and $R_5$ are independently H, an alkyl group, an aromatic group, or mixtures thereof, (2) at least one $R_1$ or $R_2$ group in this formula must not be hydrogen, and (3) most importantly, primary carbamate group X must be attached to a carbon atom having a lower degree of substitution than the carbon atom to which functional group Z is attached.

In general, the monomeric reactive compound (2) of the invention may comprise one or more structures that satisfy the above requirements. In a preferred embodiment, the monomeric reactive compound (2) will comprise at least two structures that are isomerically different as defined above but which each satisfy the above noted requirements of the invention. In a most preferred embodiment of the invention, the reactive compound of the invention will comprise at least four structures.

As noted above, it is an aspect of the invention that primary carbamate group X be attached to a carbon atom having a lower degree of substitution than the carbon atom to which functional group Z is attached. The term "lower degree of substitution" may be understood per the following statements. If X is a primary carbamate group attached to a primary carbon atom (i.e., X—$CH_2$—), Z will be functional group attached to either a secondary carbon atom (i.e., -Cn-CH(Z)-Cn'-) or a tertiary carbon atom (i.e., -Cn-$CR_0$(Z)-Cn'- wherein $R_0$ is not hydrogen and is an alkyl or aromatic containing group as further defined herein. If X is a primary carbamate group attached to a secondary carbon atom, i.e., (X—CHR—, wherein R is either $R_1$ or $R_2$ as defined above but is not hydrogen), Z must be a functional group attached to a tertiary carbon (i.e., -Cn-$CR_0$(Z)-Cn'- wherein $R_0$ is as defined above but is not hydrogen). It can be appreciated that because primary carbamate group X must be attached to a carbon atom having at least one fewer non-hydrogen substituent than that of the carbon atom to which functional group Z is attached, at least one of the substituents $R_1$ and $R_2$ must be hydrogen for the carbon to which X is attached.

Monomeric reactive compounds (2) will have one and only one primary carbamate group as defined above. That is, the reactive compound (2) used in the instant method of making the primary carbamate functional ethylenically unsaturated monomers are limited to mono-carbamate functional compounds having at least one additional functional group that is either secondary or tertiary.

Monomeric reactive compounds (2) suitable for use herein will be substantially free of heteroatoms. "Heteroatoms" as used herein refers to atoms other than carbon or hydrogen. The phrase "substantially free of" as used herein means that the portion of monomeric reactive compound (2) which does not include the primary carbamate group X or the secondary or tertiary functional group Z will generally have no more than two atoms which are other than carbon or hydrogen, i.e., atoms such as N, O, Si, mixtures thereof, and the like. More preferably, that portion of monomeric reactive compound (2) that does not include primary carbamate group X or tertiary or secondary functional group Z will have no more than one atom that is other than carbon or hydrogen. In a most preferred embodiment, that portion of monomeric reactive compound (2) that does not include functional groups X and Z will have no heteroatoms, i.e., will consist solely of carbon and hydrogen atoms. Thus, in a most preferred aspect of the invention, the only heteroatoms in monomeric reactive compound (2) will be present in functional groups X and Z.

Functional group Z will be a hydroxyl group, a halide group or a functional derivative of a hydroxy group or a halide group. A "functional derivative of a hydroxy group or halide group" refers to a reactive functional group resulting from the reaction of a hydroxy or halide functional group Y, discussed below, with another functional group. A "reactive functional group" is a functional group that is reactive with functional group (i) of the ethylenically unsaturated monomer (1). Illustrative functional derivatives of hydroxy or halide groups include acid groups, epoxy groups, cyclic carbonate groups, silane groups, isocyanate groups, primary amine groups, secondary amine groups, silicon hydrides, alkenes, organometallic groups, mixtures thereof, and the like. Hydroxyl groups are most preferred for use as functional group Z.

It will be appreciated that functional group Z is not located on a primary carbon atom in the above formula. Rather, functional group Z will be a secondary functional group when $R_0$ is H and will be a tertiary functional group when $R_0$ is an alkyl or aromatic containing group, i.e., an aliphatic group, a cycloaliphatic group, an aromatic group, or mixtures thereof. In a most preferred embodiment Z will be a secondary functional group and $R_0$ will be hydrogen.

In general, $R_0$, $R_1$, $R_2$, $R_3$, $R_4$ and $R_5$ are as defined above for the primary carbamate functional ethylenically unsaturated monomer.

As noted above, because primary carbamate group X must be attached to a carbon atom having a lower degree of substitution than the carbon atom to which functional group Z is attached, at least one of the substituents $R_1$ and $R_2$ must be hydrogen for the carbon to which X is attached. This requirement is consistent with the requirement that at least one $R_1$ or $R_2$ group must be selected from the group consisting of aliphatic groups, cycloaliphatic groups, aromatic groups and mixtures thereof. When n is 2 and $R_0$ is not hydrogen, the at least one $R_1$ or $R_2$ group that is not hydrogen may be a substituent of the carbon immediately adjacent to the carbon attached to the primary carbamate group X. That is, the carbon to which the carbamate group is attached may have a primary or secondary degree of substitution. When n is greater than 2 and $R_0$ is not hydrogen, the at least one $R_1$ or $R_2$ group that is not hydrogen may be a substituent of the carbon to which the carbamate group is attached or to any of the carbons between the carbon attached to the primary carbamate group X and the carbon attached to the functional group Z, i.e., the $C_n$ carbons.

However, it is preferred that the at least one $R_1$ or $R_2$ group which is not hydrogen be attached to a carbon not directly attached to the carbamate group X. More preferably, the at least one $R_1$ or $R_2$ group that is not hydrogen will preferably be attached to a carbon atom located in closer proximity to functional group Z rather than functional X. When n is two, it will be appreciated that the at least one $R_1$ or $R_2$ group which is not hydrogen will most preferably be attached to a carbon atom located an equal distance between the carbons to which the functional groups X and Z are attached. When n is three or greater, the at least one $R_1$ or $R_2$ group which is not hydrogen will most preferably be attached to the carbon atom which is adjacent to the carbon atom to which the functional group Z is attached or be in closer proximity thereto than to the carbon atom to which functional group X is attached.

n and n' are as defined above with respect to the primary carbamate functional ethylenically unsaturated monomer of the invention.

In a most preferred embodiment, the monomeric reactive compounds (2) used herein will be made by a particular method. It is a particular advantage of the method of the invention used to make the monomeric reactive compound (2) that in the resulting reaction product substantially all of the structures therein possess a primary carbamate group X attached to a carbon atom having a lower degree of substitution than the carbon atom to which functional group Z is attached. It is a particular disadvantage of prior art processes that they fail to provide such a reaction product. Moreover, it is a most preferred aspect of the instantly disclosed method of making the primary carbamate functional ethylenically unsaturated monomers of the invention, that only monomeric reactive compounds (2) made by this particular method are utilized.

As used herein, "substantially" refers to no more than 10% of the resulting mono-carbamate functional reaction product, i.e., the monomeric reactive compound (2), having a primary carbamate group attached to a carbon atom having a degree of substitution that is equal to or higher than that of the carbon atom to which the Z functional group is attached, preferably no more than 7%, and most preferably no more than 3%. It will be appreciated that amounts of unreacted starting materials are not part of this calculation.

The method of the invention requires that the monomeric reactive compounds (2) of the invention be made by reacting a compound (a) and a compound (b).

Compound (a) must have a functional group $F_i$ and a functional group $F_{ii}$ separated by at least three carbon atoms, wherein said functional groups $F_i$ and $F_{ii}$ are independently selected from the group consisting of functional groups convertible to primary carbamate groups, and functional group $F_i$ is attached to a carbon atom having a lower degree of substitution than a carbon atom to which functional group $F_{ii}$ is attached.

Functional groups $F_i$ and $F_{ii}$ are each independently selected from the group of functional groups convertible to primary carbamate groups. Preferred examples of functional groups $F_i$ and $F_{ii}$ convertible to primary carbamate groups are hydroxy groups and halide groups. Suitable halide groups include chloride, bromide, and iodide, with chloride being the most favored halide. Most preferably functional groups $F_i$ and $F_{ii}$ will be hydroxyl groups.

Suitable compounds (a) may include polyols, diols, polyhalides, and dihalides. However, the use of diols and dihalides as compound (a) is especially preferred as they are the most commercially available and economically feasible. Diols are most preferred for use as compound (a). Indeed, it is a particular benefit of the invention that it provides an economical and commercially feasible method of making thermally stable mono-carbamate compounds containing at least one functional group from compound (a) starting materials selected from the group consisting of dihalides and diols.

In a most preferred embodiment, compound (a) will be selected from the group of diols and dihalides of the following formula:

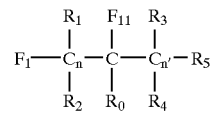

wherein $F_i$ and $F_{ii}$ are hydroxy or halide functional groups, n is an integer of 2 or more, n' is an integer of 1 or more, and $R_0$, $R_1$, $R_2$, $R_3$, $R_4$ and $R_5$ may individually be H or a group selected from the group of $C_1$–$C_{16}$ aliphatic groups, cycloaliphatic groups, aromatic groups, and mixtures thereof. However, it is an aspect of the invention that at least one $R_1$ or $R_2$ group be selected from the group consisting of $C_1$–$C_{16}$ aliphatic groups, cycloaliphatic groups, aromatic groups, and mixtures thereof. Functional group $F_i$ must be attached to a carbon atom having a lower degree of substitution than that of the carbon atom to which functional group $F_{ii}$ is attached.

Thus, it is an important aspect of the method of the invention that in compound (a), functional group $F_i$ will be attached to a carbon atom having a lower degree of substitution than the carbon atom to which functional group $F_{ii}$ is attached. For example, if $F_i$ is a primary functional group attached to a primary carbon atom (i.e., X—$CH_2$—), $F_{ii}$ will be functional group attached to either a secondary carbon atom (i.e., —$C_n$—$CH(F_n)$—$C_{n'}$—) or a tertiary carbon atom (i.e., —$C_{ii}$—$CR_0(F_{ii})$—$C_n$— wherein $R_0$ is not hydrogen and is as defined above). If $F_i$ is a primary functional group attached to a secondary carbon atom, i.e., (X—CHR—, wherein R is either $R_1$ or $R_2$ as defined above but is not hydrogen), $F_{ii}$ must be a functional group attached to a tertiary carbon, (i.e., —$C_n$—$CR_0(F_{ii})$—C— wherein $R_0$ is not hydrogen and is as defined above). It can be appreciated that because functional group $F_i$ must be attached to a carbon atom having a lower degree of substitution than the carbon atom to which functional group $F_{ii}$ is attached, at least one of the substituents $R_1$ and $R_2$ on the carbon to which $F_i$ is attached must be hydrogen.

Most preferred compounds (a) will be substantially free of heteroatoms. "Heteroatoms" as used herein refers to atoms other than carbon or hydrogen. The phrase "substantially free of" as used herein means that the portion of compound (a) which does not include the functional groups $F_i$ and $F_{ii}$ will generally have no than two atoms which are other than carbon or hydrogen, i.e., atoms such as N, O, Si, mixtures thereof, and the like. More preferably, that portion of compound (a) that does not include functional groups $F_i$ and $F_{ii}$ will have no more than one atom that is other than carbon or hydrogen. In a most preferred embodiment, that portion of compound (a) that does not include functional groups $F_i$ and $F_{ii}$ will have no heteroatoms, i.e., will consist solely of carbon and hydrogen atoms. Thus, in a most preferred aspect of the invention, the only heteroatoms in compound (a) will be present in functional groups $F_i$ and $F_{ii}$.

It will be appreciated that functional group $F_{ii}$ is not located on a primary carbon atom in the above formula. Rather, functional group $F_{ii}$ will be a secondary functional group when $R_0$ is H and will be a tertiary functional group when $R_0$ is not hydrogen and is selected from the group of aliphatic groups, cycloaliphatic groups, aromatic groups, or mixtures thereof. In a most preferred embodiment $F_{ii}$ will be a secondary functional group and $R_0$ will be hydrogen.

In general, $R_0$, $R_1$, $R_2$, $R_3$, $R_4$ and $R_5$ are as defined above with respect to the primary carbamate functional ethylenically unsaturated monomer of the invention.

As noted above $R_0$ may be H or an alkyl or aromatic containing group or mixtures thereof. In a most preferred embodiment $R_0$ will be H so that functional group $F_{ii}$ is a secondary functional group. If $R_0$ is not hydrogen, suitable groups are those groups selected from the group of aliphatic groups, cycloaliphatic groups, aromatic groups and mixtures thereof. Preferred for use as $R_0$ are aliphatic and cycloaliphatic groups, with aliphatic groups being most preferred for use as $R_0$ Particularly suitable groups for use as $R_0$ are aliphatic groups and cycloaliphatic groups containing from one to sixteen carbon atoms, with aliphatic groups containing one to twelve carbon atoms being preferred if $R_0$ is an alkyl group and aliphatic groups containing one to eight carbon atoms being most preferred if $R_0$ is an alkyl group. Finally, it is within the scope of the invention that $R_0$ be an alkyl or aromatic group connected to any of the other $R_{1-5}$ substituents.

It is an aspect of the invention that at least one $R_1$ or $R_2$ group must be selected from the group consisting of aliphatic groups, cycloaliphatic groups, and aromatic groups. That is, at least one of the $R_1$ and $R_2$ substituent groups must be other than hydrogen so long as functional group $F_i$ is attached to a carbon atom having a lower degree of substitution than the carbon atom to which functional group $F_{ii}$ is attached. Illustrative groups suitable for use as the $R_1$ or $R_2$ groups that are not hydrogen are those as defined above for $R_0$. Preferred for use as $R_1$ and $R_2$ are aliphatic and cycloaliphatic groups, with aliphatic groups being most preferred for use as $R_1$ or $R_2$ if they are not hydrogen Particularly suitable non-hydrogen groups for use as $R_1$ and $R_2$ are aliphatic groups and cycloaliphatic groups containing from one to sixteen carbon atoms, with aliphatic groups containing from one to twelve carbon atoms being preferred if $R_1$ or $R_2$ is an alkyl group and aliphatic groups containing one to eight carbon atoms being most preferred if $R_1$ or $R_2$ is an alkyl group. Finally, it is within the scope of the invention that $R_1$ or $R_2$ be an alkyl or aromatic group connected to any of the other $R_{0, 3-5}$ substituents.

As noted above, because functional group $F_i$ must be attached to a carbon atom having a lower degree of substitution than the carbon atom to which functional group $F_{ii}$ is attached, at least one of the substituents $R_1$ and $R_2$ must be hydrogen for the carbon to which $F_i$ is attached. This requirement is consistent with the requirement that at least one $R_1$ or $R_2$ group must be selected from the group consisting of aliphatic groups, cycloaliphatic groups, aromatic groups and mixtures thereof. When n is 2 and $R_0$ is not hydrogen, the at least one $R_1$ or $R_2$ group that is not hydrogen may be a substituent of the carbon immediately adjacent to the carbon attached to the primary carbamate group X. That is, the carbon to which the carbamate group is attached may have a primary or secondary degree of substitution. When n is greater than 2 and $R_0$ is not hydrogen, the at least one $R_1$ or $R_2$ group that is not hydrogen may be a substituent of the carbon to which the carbamate group is attached or to any of the carbons between the carbon attached to the functional group $F_i$ and the carbon attached to the functional group $F_{ii}$, i.e., the $C_n$ carbons.

However, it is preferred that the at least one $R_1$ or $R_2$ group which is not hydrogen be attached to a carbon not directly attached to the functional group $F_i$. More preferably, the at least one $R_1$ or $R_2$ group that is not hydrogen will preferably be attached to a carbon atom located in closer proximity to functional group $F_{ii}$ rather than functional group $F_i$. When n is two, it will be appreciated that the at least one $R_1$ or $R_2$ group which is not hydrogen will most preferably be attached to a carbon atom located an equal distance between the carbons to which the functional groups $F_i$ and $F_{ii}$ are attached. When n is three or greater, the at least one $R_1$ or $R_2$ group which is not hydrogen will most preferably be attached to the carbon atom which is adjacent to the carbon atom to which the functional group $F_{ii}$ is attached or be in close proximity thereto than to the carbon atom to which the functional group $F_i$ is attached.

n and n' are as defined above for the primary carbamate functional ethylenically unsaturated monomer of the invention.

Illustrative compounds (a) for use in a preferred embodiment of the method of the invention include 2-ethyl-1,3 hexanediol, 2-methyl-2,4-pentane diol, 2,2,4-trimethyl-1,3-pentanediol, 2,4-diethyl-1,5-octanediol, 1-hydroxymethyl cyclohexan-4-ol, and all those isomers thereof which satisfy the above requirements of the preferred formula for compound (a).

"Isomers" as used herein refers to structural and position isomers that have the same empirical chemical formula. An illustrative example of some structural isomers would be 2-ethyl-1,3-hexanediol and 2-propyl-1,3-pentanediol. An illustrative example of a position isomer would be 2-ethyl-1,3-hexanediol and 2-ethyl-1,4-hexanediol. An illustrative example of isomers which are both structural and position isomers would be 2-ethyl-1,3-hexanediol and 2-propyl-1,4-pentanediol. However, it will be appreciated that only those isomers that satisfy the requirements of the instant invention are suitable, i.e., they must (1) be of the formula:

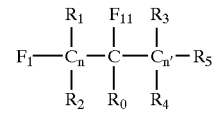

wherein $F_i$ and $F_{ii}$ are either hydroxy groups or halide groups, n is an integer of 2 or more, n' is an integer of 1 or more, and $R_0$, $R_1$, $R_2$, $R_3$, $R_4$ and $R_5$ are independently H, an alkyl group, an aromatic group, or mixtures thereof, (2) at least one $R_1$ or $R_2$ group in this formula must not be hydrogen, and (3) most importantly, functional group $F_{ii}$ must be attached to a carbon atom having a lower degree of substitution than the carbon atom to which functional group $F_{ii}$ is attached.

In one preferred embodiment, compound (a) will be selected from those members of the preferred formula for compound (a) that possess a particularly preferred isomeric distribution. 'Isomeric distribution' as used herein refers to the number of individual isomers that make up the material. A particularly preferred isomeric distribution is one in which compound (a) is a mixture of isomers having at least 4 or more individual isomers or structures. The resulting products made according to the invention from these materials have a greater tendency of being non-crystalline in nature. This is of advantage obtaining primary carbamate functional acrylic polymers suitable for use in providing low VOC curable coating compositions.

However, it will be appreciated that even compounds (a) consisting of one structure or isomer will provide acceptable levels of performance with respect to low VOC coatings. While not wishing to be bound to a particular theory, it is believed that this is attributable to the low degree of symmetry found in particular compounds (a) and thus in the monomeric reactive compounds (2) used in the instant invention.

It will be appreciated that the selection of compound (b) is somewhat dependent upon the selection of functional groups $F_i$ and $F_{ii}$ of compound (a). In general, if functional group ($F_i$) is a hydroxyl group, it will be converted into a primary carbamate by reaction with a compound (b) selected from the group consisting of alkyl carbamates, cycloalkyl carbamates, ether carbamates, beta hydroxy alkyl carbamates, aryl carbamates, cyanic acid produced, for example, by the decomposition of urea, and phosgene followed by reaction with ammonia. If functional group ($F_i$) is a halide group, it may be converted into a primary carbamate group by reaction with a metal carbamate such as silver carbamate as discussed in P. Adams & F. Baron, "Esters of Carbamic Acid", Chemical Review, v. 65, 1965. In a preferred embodiment, compound (b) will be selected from the group of alkyl carbamates, cycloalkyl carbamates, ether carbamates and aryl carbamates, and mixtures thereof, with alkyl carbamates being most preferred as compound (b).

Illustrative alkyl carbamates, cycloalkyl carbamates, and aryl carbamates include methyl carbamate, propyl carbamate, n-butyl carbamate, cyclohexyl carbamate, t-butyl carbamate, isopropyl carbamate, and phenyl carbamate. An example of a hydroxyalkyl carbamate is hydroxyethyl carbamate. An example of an ether carbamate is 2-methoxyethyl carbamate. It will be appreciated that when (b) is selected from these compounds, reaction with suitable compounds (a) results in alcohols, phenols, ether alcohols and related materials as by-products. Examples of most preferred alkyl carbamates for use as compound (b) include methyl carbamate, isopropyl carbamate and n-butyl carbamate.

Compound (a) and compound (b) are reacted under conditions intended to minimize the formation of functional group ($F_{ii}$) to a carbamate group. In general, compounds (a) and (b) will reacted under conditions such that no more than 10% of the functional group (ii) is converted to a carbamate group, based on the starting amount of compound (a). More preferably, compounds (a) and (b) will be reacted under conditions such that no more than 5% of functional group ($F_{ii}$) is converted to a carbamate group, and most preferably no more than 4% of functional group ($F_{ii}$) will be converted to a carbamate group, all based on the starting amount of compound (a).

Thus, the formation of dicatbamate species is highly disfavored in the method of the invention. One technique to disfavor the formation of the dicarbamate is to use a deficit amount of compound (b), that is, the equivalent of the functional groups of compound (b) is less than the equivalent amount of functional group $F_i$ based on the starting amount of compound (a). In this case, the equivalent amount of compound (b) used in relationship to functional group $F_i$ can range from 0.99:1 to 0.25:1. An alternative technique that can be used to disfavor the formation of the dicarbamate when one or more than one equivalent of compound (b) are used in comparison to functional group $F_i$ on compound (a) is to stop the reaction before all of functional $F_i$ is converted to a primary carbamate. This second technique works best for reaction conditions that have a high degree of selectivity such as transcarbamation reactions. In comparison, this technique would be disfavored in a more nonselective reaction such as that between a hydroxy group and cyanic acid.

While not wishing to be bound to a particular theory, it is believed that the effectiveness of these two approaches can be increased by increasing the relative degree of steric hindrance surrounding functional groups $F_i$ and $F_{ii}$ on compound (a). That is, in general, dicarbamate formation can be diminished if the degree of steric hindrance surrounding functional group $F_{ii}$ is greater than the degree of steric hindrance on functional group $F_i$. This relationship is believed to hold true regardless of the method of reaction selected.

If not all of functional group $F_i$ has been transformed into a primary carbamate, the excess amount of unreacted starting material (a) can be removed by known techniques, such as vacuum distillation, extraction or filtration or may be left in as discussed below.

In some cases, the presence of unreacted (a) in the monomeric reactive compound (2) may be desirable in the reaction processes used to make the primary carbamate functional ethylenically unsaturated monomers of the invention. For example, unreacted monomeric reactive compound (2) may be utilized in the formation of di or polyacrylate monomers. However, it is preferred that any excess amount of unreacted (a) be removed before the formation of the primary carbamate functional ethylenically unsaturated monomers of the invention.

It will be appreciated that the reaction of compounds (a) and (b) produces a reactive compound of the formula:

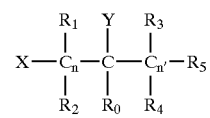

wherein X is a primary carbamate group, Y is a hydroxy or halide group, n is an integer of 2 or more, n' is an integer of 1 or more, and $R_0$, $R_1$, $R_2$, $R_3$, $R_4$ and $R_5$ may be independently H or a group selected from aliphatic groups, cycloaliphatic groups, aromatic groups and mixtures thereof, with the provisos that (i) at least one of the $R_1$ and $R_2$ groups is not hydrogen, and (ii) primary carbamate group X is attached to a carbon atom having a lower degree of substitution than a carbon atom to which functional group Y is attached.

While this reactive compound containing functional group Y can be used directly as the monomeric reactive compound (2) of the invention, it can also be used as a precursor to form monomeric reactive compound (2) containing functional group Z. While both functional group Z and functional group Y may be either a hydroxy group or a halide group, functional group Z may also be selected from the group consisting of functional derivatives of hydroxy groups and halide groups. As discussed above, functional derivatives of hydroxy groups and halide groups are those reactive functional groups resulting from single or multistep reactions of a hydroxy or halide group with one or more functional groups. Illustrative derivatives of hydroxy or halide groups include acid groups, epoxy groups, cyclic carbonate groups, silane groups, isocyanate groups, amine groups especially primary and secondary amines, silicon hydrides, alkenes, organometallics, mixtures thereof, and the like.

Examples of suitable functional group reactants used to obtain particular functional derivatives of either hydroxy groups or halide groups are illustrated in the following table. It should be noted that the recitation of more than one reactant refers to a multistep reaction process wherein the first functional derivative of Y is subsequently reacted with the next reactant to make the next or desired functional derivative of Y. It is within the scope of this invention for suitable functional groups used in the conversion of Y to Z to be part of the ethylenically unsaturated monomer (1) used in the instant invention. Indeed, as discussed below, in one embodiment, an ethylenically unsaturated monomer (1) having appropriate functionality as discussed herein and in the table below, may be used as the "Reactant(s)" of the table below to provide the primary carbamate functional ethylenically unsaturated monomer of the invention.

| Functional Group Y | Reactant(s) | Functional Derivative of Y |
|---|---|---|
| OH | diisocyanate | isocyanate |
| OH | cyclic anhydride | acid |
| OH | epoxy | alcohol |
| OH | methacrylic acid | alkene |
| OH | methacrylic anhydride | alkene |
| OH | silicone hydride | silane |
| halide (Cl, Br, F, or I) | ammonia | primary amine |
| halide (Cl, Br, F, or I) | primary amine | secondary amine |
| halide (Cl, Br, F, of I) | alkali and alkali earths metals (Mg, Na, Li) | organometallics |
| halide (Cl, Br, F, or I) | alkali earth metal/allyl iodide/peroxide/ carbon dioxide | organometallic/alkene/ epoxy/cyclic carbonate |
| halide (Cl, Br, F, or I) | ammonia/phosgene | primary amine/isocyanate |
| halide (Cl, Br, F, or I) | alkali and alkali earth/ ketone | organometallic/hydroxy |

It will be appreciated that a hydroxy group or halide group may be an original functional group Y or may be a derivative resulting from one or more derivative reactions. For example, a halide group Y may be converted into a hydroxy group by an initial reaction with an alkali or alkali earth to produce an organometallic followed by subsequent reaction of the organometallic with a ketone to provide a hydroxy group. However, those of skill in the art will appreciate that a 'derivative' hydroxy group will be different in structure than an 'original' hydroxy group. In particular, the 'derivative' hydroxy group will now contain the reaction product residue from the derivatization reaction processes, i.e., in this case, a ketone backbone will remain. Such reaction product residues may or may not contain additional functionality suitable for subsequent conversions or reactions. If such additional reactive functional groups are present in the reaction product residue, they are considered to be within the definition of functional derivative groups of hydroxy or halide groups.

In general, it is preferred that original hydroxy groups or halide groups Y be used as functional group Z if Z is hydroxy or halide.

It will be appreciated that the foregoing examples are illustrative only and that many other variations in reactants and reaction processes can be used to obtain desirable functional derivatives of halide or hydroxy groups, especially with regards to multistep reaction processes. Moreover, the use of various catalysts, work-up reagents, initiators, and reaction conditions in the foregoing reaction processes are held to be within the knowledge and experience of those of ordinary skill in the art.

The ethylenically unsaturated monomer (1) must comprise one or more functional groups (i) which are reactive with a functional group Z as defined above but which are substantially nonreactive with a primary carbamate group X of monomeric reactive compound (2).

In general, the ethylenically unsaturated monomer (1) is a hydrocarbon-based material that may or may not, but will preferably not, contain heteroatoms in those portions of the monomer (1) not including linking group L, functional group (i) and any optional functional groups. "Heteroatoms" as used herein refers to atoms other than carbon or hydrogen. Preferred heteroatoms are O, N, Si, and mixtures thereof.

As used herein, the term "ethylenically unsaturated monomer" refers to a material that does not contain two or more of the same repeating units. The term "repeating units" as defined as herein refers to groups of atoms that are the reaction product result or residue of the reaction of two or more monomers. In general, ethylenically unsaturated monomers (1) suitable for use in the instant invention will have number average molecular weights in the range of from 55 to 2000 Daltons, more preferably in the range of from 55 to 750 Daltons, and most preferably in the range of from 128 to 750 Daltons.

The ethylenically unsaturated monomer (1) must comprise one or more functional groups (i) which are reactive with a functional group Z but which are substantially nonreactive with a primary carbamate group X of monomeric reactive compound (2).

"Substantially nonreactive" as used herein refers to a reactive functional group (i) which does not react with the primary carbamate group under the conditions in which the ethylenically unsaturated monomer (1) is reacted with monomeric reactive compound (2). In general, no more than 7% of primary carbamate group X will be reacted, preferably no more than 5%, and most preferably no more than 3% of primary carbamate group X will be reacted, based on the starting amount of monomeric reactive compound (2).

In general, functional groups (i) are those functional groups that are reactive with a functional group Z as defined above. Suitable functional groups (i) will thus encompass all functional groups reactive with either hydroxy groups, halide groups or any derivatives thereof as defined above. Illustrative functional groups (i) include hydroxy groups, cyclic anhydrides, anhydride groups, carboxylic acid groups, epoxy groups, cyclic carbonate groups, organometallic materials such as sodium or lithium alkanes, metal alkoxides, silane groups, isocyanate groups, primary amine groups, secondary amine groups, silicon hydrides, alkenes, mixtures thereof, and the like. Preferred functional groups (i) are carboxylic acid groups, isocyanates, cyclic anhydrides, anhydrides, epoxy groups, oganometallic groups, hydroxy groups, and mixtures thereof. Most preferred functional groups (i) are isocyanate groups, anhydride groups, acid groups, and mixtures thereof.

In addition to required functional group (i), the ethylenically unsaturated monomer (1) may optionally comprise one or more additional functional groups (ii), different from required functional group (i). In general, optional functional group (ii) may be defined as any reactive functional group that is reactive with a reactive functional group of a curing agent (B). Illustrative examples include all of those reactive functional groups discussed above in regards to functional group Z and functional group (i).

Examples of suitable ethylenically unsaturated monomers suitable for use as monomer (1) include all ethylenically unsaturated monomers comprising a functional group (i) that can be used to react with a functional group Y or Z as described above.

For example, illustrative functional groups (i) such as, isocyanate, epoxy, cyclic carbonate, or anhydride can be incorporated into the ester portion of the acrylic monomer. For example, isocyanate functional acrylic monomers that can be used to react with monomeric reactive compound (2) include isocyanato ethyl methacrylate, glycidyl methacrylate, (2-oxo-1,3-dioxolan-4-yl)methyl methacrylate, and the like. Other acrylic monomers having functional groups (i) in the ester portion of the monomer are also within the skill of the art. Other illustrative examples of suitable ethylenically unsaturated monomers (1) include (methyl) acrylic acid and its anhydride, glycidyl methacrylate, hydroxy butyl acrylate, 2-oxo-1,3-dioxolan-4-yl)methyl methacrylate, isocyanato ethyl acrylate, and maleic anhydride. Organometallic complexes of (meth) acrylic acid such as sodium methacrylate may be used wherein functional group (i) is a alkali or alkali earth metal.

The ethylenically unsaturated monomer (1) and monomeric reactive compound (2) are reacted together in the method of the invention to make the primary carbamate functional ethylenically unsaturated monomers of the invention discussed above. In general, the reaction conditions suitable for use herein will be known and recognized to those of ordinary skill in the art.

Not withstanding this, it should be appreciated that it is an advantage of the method of the invention that the monomeric reactive compound (2) can be subjected to harsher reaction conditions than may be used with other monocarbamate functional reactive compounds of the prior art. For example, reaction temperatures of greater than 140° C. may be used without any appreciable decomposition of monomeric reactive compound (2) occuring. In addition, the monomeric reactive compound (2) used in the method of the invention may be subjected to strong acid or basic reaction conditions.

In a most preferred embodiment, the methods of the invention will utilize the monomeric reactive compound (2) produced by the method of making monomeric reactive compound (2) disclosed above.

The primary carbamate functional acrylic polymers and/or oligomers of the invention will result from the polymerization of a monomer mixture comprising the particular primary carbamate functional ethylenically unsaturated monomer of the invention discussed above.

In general, the monomer mixture to be polymerized will comprise from 2 to 100% by weight of the particular primary carbamate functional ethylenically unsaturated monomer of the invention, more preferably from 40 to 100% by weight, and most preferably, from 80 to 100% by weight, all based on the total weight of the monomer mixture to be polymerized.

It will therefore be appreciated that the monomer mixture to be polymerized may comprise ethylenically unsaturated monomers other than the primary carbamate functional ethylenically unsaturated monomer of the invention. These "other" ethylenically unsaturated monomers may be functional or nonfunctional ethylenically unsaturated monomers. For example, other ethylenically unsaturated monomers that may be used in the monomer mixture to be polymerized include all those ethylenically unsaturated monomers typically used in acrylic polymerizations.

Illustrative examples of other ethylenically unsaturated monomers having no reactive functional groups include monomers such as alkyl vinyl materials such as methyl acrylate, methyl methacrylate, butyl methacrylate, cycloaliphatic vinyl materials such as cyclohexyl methacrylate, aromatic vinyl materials such as styrene and alpha-methyl styrene, and the like.

Such nonfunctional ethylenically unsaturated monomers may be used in the monomer mixture in amounts of from 0 to 98% by weight, more preferably from 0 to 60% by weight, and most preferably from 0 to 20% by weight, all based on the total weight of the monomer mixture to be polymerized.

Illustrative examples of ethylenically unsaturated monomers comprising reactive functional groups include acrylic acid, methacrylic acid, and their functional esters such as hydroxy-functional acrylic monomers including hydroxyethyl acrylate, hydroxybutyl acrylate, hydroxybutyl methacrylate, hydroxypropyl acrylate, and the like, and epoxy functional esters such as glycidyl methacrylate and the like. Amino-functional acrylic monomers would include t-butylaminoethyl methacrylate and t-butylaminoethylacrylate. Lactone extended monomers such as the reaction product of hydroxy ethyl acrylate with ε-caprolatone are also suitable for use in the monomer mixture as the "other" ethylenically unsaturated monomer. Other acrylic monomers having active hydrogen functional groups in the ester portion of the monomer are also within the skill of the art.

Such functionally reactive ethylenically unsaturated monomers may be used in the monomer mixture to be polymerized in amounts of from 0 to 98% by weight, more preferably from 0 to 60% by weight, and most preferably from 0 to 20% by weight, all based on the total weight of the monomer mixture to be polymerized.

The monomer mixture to be polymerized may be polymerized using conventional polymerization techniques wherein chains terminate when reactive intermediates are destroyed or rendered inactive, such as free radical polymerization, cationic polymerization, or anionic polymerization, in, for example, a batch or semi-batch process. Free radical polymerization processes are most preferred. For instance, the polymerization may be carried out by heating the ethylenically unsaturated monomers in bulk or in organic solution or aqueous dispersion in the presence of a free radical source, such as an organic peroxide or azo compound and, optionally, a chain transfer agent for a batch process; or, alternatively, the monomers and initiator(s) may be fed into the heated reactor at a controlled rate in a semi-batch process.

Typical free radical sources are organic peroxides such as dialkyl peroxides, peroxyesters, peroxydicarbonates, diacyl peroxides, hydroperoxides, and peroxyketals; and azo compounds such as 2,2'-azobis(2-methylbutanenitrile) and 1,1'-azobis(cycohexanecarbonitrile). Typical chain transfer agents are mercaptans such as octyl mercaptan, n- or tertdodecyl mercaptan, thiosalicyclic acid, mercaptoacetic acid, and mercaptoethanol; halogenated compounds, and dimeric alpha-methyl styrene.

The free radical polymerization is usually carried out at temperatures from about 20° C. to about 200° C., preferably from 90° C. to 170° C. The reaction may conveniently be done at the temperature at which the solvent or solvent mixture refluxes, although reflux is not necessary to the reaction. The initiator should be chosen to match the temperature at which the reaction is carried out, so that the half-life of the initiator at the reaction temperature should preferably be no more than thirty minutes.

If solvents are used in the polymerization reaction, the solvents used are preferably water or water-soluble or -miscible organic solvents that can function as cosolvents. A cosolvent is useful to aid in dispersion of the components and in flow during cure of the composition. Examples of useful solvents include methyl ethyl ketone, methyl isobutyl ketone, xylene, n-amyl acetate; and cosolvents such as N-methylpyrrolidone and glycol ethers like ethylene glycol butyl ether, ethylene glycol butyl ether acetate, diethylene glycol butyl ether, ethylene glycol 2-ethylhexyl ether, propylene glycol methyl ether, propylene glycol methyl ether acetate, propylene glycol butyl ether, and dipropylene glycol butyl ether.

The solvent or solvent mixture is generally heated to the reaction temperature and the monomers and initiator(s) used to make the stabilizing resin (P1) are added at a controlled rate over a period of time, usually between 2 and 6 hours. A chain transfer agent or additional solvent may be added concurrently with the monomers and initiator(s). The mixture is usually held at the reaction temperature after the additions for a period of time to complete the reaction.

Optionally, additional initiator may be added during the latter stages of the addition or after the addition is completed, usually over a period of one to sixty minutes, to ensure complete conversion.

Alternatively, the monomer mixture comprising the primary carbamate functional ethylenically unsaturated monomer of the invention may be polymerized using controlled or living radical polymerization processes as described by Matyjaszewski and Krysztof in Chem. Reviews, Vol. 101 pg 2921–2990 (2001), or by iniferter process as described by Kuchanov, in J. of Polymer Science, Part A: Polymer Chemistry Vol 32 pg 1557–1568 (1994), and Gaofenzi Xuebao Vol 2 pg 127–136 (2002), nitroxide-mediated polymerization as described by Zaremski, in Russian Polymer News Vol 4 pg 17–21 (1999), and Wang, in Abstracts of Papers, 224th ACS National Meeting, Boston, Mass., United States, Aug. 18–22, 2002 (2002), all of which are incorporated by reference herein.

In addition to normal thermo process, the monomer mixture comprising the primary carbamate functional ethylenically unsaturated monomer of the invention may be polymerized using the aid of ultrasound as described by Orszulik in Polymer Vol 34, pg 1320–1 (1993), or by UV light.

The primary carbamate functional acrylic polymers of the invention resulting from the polymerization of the monomer mixture will comprise comprising randomly repeating units of the formula:

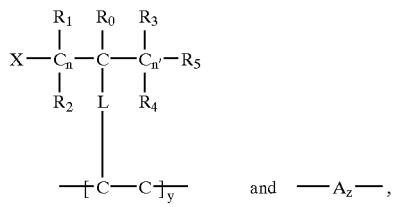

wherein X is a primary carbamate group, n is an integer of 2 or more, n' is an integer of 1 or more, $R_0$, $R_1$, $R_2$, $R_3$, $R_4$ and $R_5$ are independently H, an alkyl group, an aromatic group, or mixtures thereof, at least one $R_1$ or $R_2$ group is not hydrogen, L is a linking group, y represents from 2 to 100% by weight, based on the total weight of all ethylenically unsaturated monomers in the monomer mixture, A represents functional or nonfunctional repeating units derived from one or more other ethylenically unsaturated monomers, z represents from 0% to 98% by weight, based on the total weight of all ethylenically unsaturated monomers in the monomer mixture, but with the proviso that substantially all primary carbamate groups X are attached to carbon atoms having a lower degree of substitution than a carbon atom to which linking group L is attached.

L is a polyvalent linking group comprising the reaction residue from the reaction between the functional group (i) of the ethylenically unsaturated monomer (1) and monomeric, reactive compound (2). It will thus be appreciated that if monomeric reactive compound (2) contained a hydroxy or halide derivative as functional group Z, linking group L may also comprise any reaction residue from the derivatization reactions converting the hydroxy or halide group Y into a hydroxy or halide derivative group Z.

Illustrative examples of polyvalent linking groups L include esters, ethers, urethanes, ureas, silanes, and the like. Preferred linking groups are urethanes, ureas, and esters with urethanes and esters being most preferred as linking group L.

As noted above, linking group L may comprise pendant functional groups. Illustrative functional groups which may be part of linking group L include hydroxy groups, primary carbamate groups, acid groups, silane groups, amide groups, isocyanate groups, epoxy groups, and the like.

y represents from 2 to 100% by weight of, based on the total weight of all ethylenically unsaturated monomers in the monomer mixture, more preferably from 40 to 100% by weight, and most preferably from 80 to 100% by weight, all based on the total weight of all ethylenically unsaturated monomers in the monomer mixture.

A represents repeating units derived from one or more functional or nonfunctional ethylenically unsaturated monomers different from the primary carbamate functional monomer of the invention. Such other ethylenically unsaturated monomers are as discussed above.

It will therefore be appreciated that z represents from 0 to 98% by weight based on the total weight of all ethylenically unsaturated monomers in the monomer mixture, more preferably from 0 to 60% by weight, and most preferably from 0 to 20% by weight, all based on the total weight of all ethylenically unsaturated monomers in the monomer mixture.

Finally, it will be appreciated that substantially all primary carbamate groups X are attached to carbon atoms having a lower degree of substitution than a carbon atom to which linking group L is attached. This relationship is the same as defined above with respect to the primary carbamate functional ethylenically unsaturated monomer, the monomeric reactive compound (2), and the compound (a).

It will be appreciated that the primary carbamate functional acrylics of the invention may be polymers or oligomers. For the purposes of the instant invention, the term "oligomer" refers to those materials having from two to nine repeating units or mixtures of repeating units. In general, illustrative acrylic oligomers of the instant invention will have number average molecular weights in the range of from 200 to 1499 Daltons. "Polymer" as used herein refers to materials having at least ten repeating units, more preferably greater than 10 repeating units. In general, acrylic polymers of the invention will have a number average molecular weight in the range of from 1500 to 1,000,000 Daltons, preferably between 1500 and 50,000 Daltons, most preferably between 1500 and 15,000 Daltons.

The curable coating compositions of the invention will comprise the primary carbamate functional acrylic oligomers and polymers of the invention as a film-forming component. In a preferred embodiment, the curable coating compositions of the invention will comprise the primary carbamate functional acrylic polymers and/or oligomers as binders (A).

The primary carbamate functional acrylic polymers and/or oligomers of the invention may comprise from 1 to 99% by weight based on total NV film-forming component, more preferably from 1 to 70% by weight, and most preferably from 5 to 50% by weight, based on total NV film-forming component.

The curable coating compositions of the invention may also comprise additional binders (A) different from the primary carbamate functional acrylic polymers and oligomers of the invention and comprising one or more active hydrogen-containing groups or groups suitable for UV or free radical cure, a curing agent (B) having one or more functional groups that are reactive with the primary carbamate functional polymers and/or oligomers of the invention or other binders (A)

Examples of suitable additional binders or polymer resins (A) having active hydrogen-containing functional groups on polymer resins are well known in the art. Such groups include, for example, hydroxyl groups, amino groups, thiol groups, hydrazide groups, activated methylene groups, and mixtures thereof. Hydroxyl groups, and mixtures thereof are most preferred hydrogen-containing functional groups.

Suitable polymer resins include, for example, acrylic polymers, modified acrylic polymers, polyesters, polyepoxides, polycarbonates, polyurethanes, polyamides, polyimides, and polysiloxanes, all of which are well known in the art. Preferably, the polymer is an acrylic, modified acrylic or polyester. More preferably, the polymer is an acrylic polymer.

In one embodiment of the invention, the polymer is an acrylic different from the acrylic polymers of the invention. The acrylic polymer preferably has a molecular weight of 500 to 1,000,000, and more preferably of 1500 to 50,000. As used herein, "molecular weight" refers to number average molecular weight, which may be determined by the GPC method using a polystyrene standard.

Acrylic polymers are well-known in the art, and can be prepared from monomers such as methyl acrylate, acrylic acid, methacrylic acid, methyl methacrylate, butyl methacrylate, cyclohexyl methacrylate, and the like. The active hydrogen-containing functional group can be incorporated into the ester portion of the acrylic monomer through the selection of a suitable ethylenically unsaturated functional monomer. For example, hydroxy-functional acrylic monomers that can be used to form such polymers include hydroxyethyl acrylate, hydroxybutyl acrylate, hydroxybutyl methacrylate, hydroxypropyl acrylate, and the like. Amino-functional acrylic monomers would include t-butylaminoethyl methacrylate and t-butylaminoethylacrylate. Other acrylic monomers having active hydrogen functional groups in the ester portion of the monomer are also within the skill of the art.

Modified acrylics can also be used as the polymer or binder (A) in the curable coating compositions of the invention. Such acrylics may be polyester-modified acrylics or polyurethane-modified acrylics, as is well known in the art. Polyester-modified acrylics modified with ε-caprolactone are described in U.S. Pat. No. 4,546,046 of Etzell et al, the disclosure of which is incorporated herein by reference. Polyurethane-modified acrylics are also well known in the art. They are described, for example, in U.S. Pat. No. 4,584,354, the disclosure of which is incorporated herein by reference.

Polyesters having active hydrogen groups such as hydroxyl groups can also be used as the binder (A) in the curable coating composition according to the invention. Such polyesters are well known in the art, and may be prepared by the polyesterification of organic polycarboxylic acids (e.g., phthalic acid, hexahydrophthalic acid, adipic acid, maleic acid) or their anhydrides with organic polyols containing primary or secondary hydroxyl groups (e.g., ethylene glycol, butylene glycol, neopentyl glycol).

Polyurethanes having active hydrogen functional groups are also well known in the art. They are prepared by a chain extension reaction of a polyisocyanate (e.g., hexamethylene diisocyanate, isophorone diisocyanate, MDI, etc.) and a polyol (e.g., 1,6-hexanediol, 1,4-butanediol, neopentyl glycol, trimethylol propane). They can be provided with active hydrogen functional groups by capping the polyurethane chain with an excess of diol, polyamine, amino alcohol, or the like.

The curable coating compositions of the invention will most preferably include one or more curing agents (B). The primary carbamate functional polymers of the invention and any optional binders (A) are cured via reaction with a component (B) having a plurality of functional groups that are reactive with the primary carbamate groups of the materials of the invention and any reactive functional groups on binder (A). Such reactive groups include active methylol or methylalkoxy groups on aminoplast crosslinking agents or on other compounds such as phenol/formaldehyde adducts, isocyanate groups, siloxane groups, cyclic carbonate groups, and anhydride groups.

Examples of compounds suitable for use as curing agent (B) include melamine formaldehyde resin (including monomeric or polymeric melamine resin and partially or fully alkylated melamine resin), blocked or unblocked polyisocyanates (e.g., TDI, MDI, isophorone diisocyanate, hexamethylene diisocyanate, and isocyanurate trimers of these, which may be blocked for example with alcohols or oximes), urea resins (e.g., methylol ureas such as urea formaldehyde resin, alkoxy ureas such as butylated urea formaldehyde resin), polyanhydrides (e.g., polysuccinic anhydride), and polysiloxanes (e.g., trimethoxy siloxane). Aminoplast resin such as melamine formaldehyde resin or urea formaldehyde resin are especially preferred.

A solvent may optionally be utilized in the curable coating compositions of the present invention. Although the composition used according to the present invention may be utilized, for example, in the form of substantially solid powder, or a dispersion, it is often desirable that the composition is in a substantially liquid state, which can be accomplished with the use of a solvent. This solvent should act as a solvent with respect to all polymeric and/or oligomeric components. In general, depending on the solubility characteristics of the polymeric components, the solvent can be any organic solvent and/or water. In one preferred embodiment, the solvent is a polar organic solvent. More preferably, the solvent is a polar aliphatic solvents or polar aromatic solvents. Still more preferably, the solvent is a ketone, ester, acetate, aprotic amide, aprotic sulfoxide, or aprotic amine. Examples of useful solvents include methyl ethyl ketone, methyl isobutyl ketone, m-amyl acetate, ethylene glycol butyl ether-acetate, propylene glycol monomethyl ether acetate, xylene, N-methylpyrrolidone, or blends of aromatic hydrocarbons. In another preferred embodiment, the solvent is water or a mixture of water with small amounts of co-solvents.

The curable coating compositions of the invention may include a catalyst to enhance the cure reaction. For example, when aminoplast compounds, especially monomeric melamines, are used as curing agent (B), a strong acid catalyst may be utilized to enhance the cure reaction. Such catalysts are well known in the art and include, for example, p-toluenesulfonic acid, dinonylnaphthalene disulfonic acid, dodecylbenzenesulfonic acid, phenyl acid phosphate, monobutyl maleate, butyl phosphate, and hydroxy phosphate ester. Strong acid catalysts are often blocked, e.g. with an amine. Other catalysts that may be useful in the composition of the invention include Lewis acids, zinc salts, and tin salts.

In a preferred embodiment of the invention, the solvent is present in the coating composition in an amount of from about 0.01 weight percent to about 99 weight percent, preferably from about 10 weight percent to about 60 weight percent, and more preferably from about 30 weight percent to about 50 weight percent.

Any additional agent used, for example, surfactants, fillers, stabilizers, wetting agents, dispersing agents, adhesion promoters, UV absorbers, HALS, etc. may be incorporated into the coating composition of the invention. While the agents are well-known in the prior art, the amount used must be controlled to avoid adversely affecting the coating characteristics.

The curable coating compositions of the invention may be used in a wide variety of applications, such as primers, basecoats, clearcoats, two-component systems, anti-chip coating compositions, water borne coatings, solvent borne coatings, coatings for flexible substrates, solventless coatings, powder coatings, and the like. In a preferred embodiment, the curable coating compositions of the invention are preferably utilized in a high-gloss coating and/or as the clearcoat of a composite color-plus-clear coating. High-gloss coatings as used herein are coatings having a 20° gloss (ASTM D523-89) or a DOI (ASTM E430-91) of at least 80.

When the coating composition of the invention is used as a high-gloss pigmented paint coating, the pigment may be any organic or inorganic compounds or colored materials, fillers, metallic or other inorganic flake matenals such as mica or aluminum flake, and other materials of kind that the art normally names as pigments. Pigments are usually used in the composition in an amount of 1% to 100%, based on the total solid weight of components A, B and C (i.e., a P:B ratio of 0.1:1.0).

When the coating composition according to the invention is used as the clearcoat of a composite color-plus-clear coating, the pigmented basecoat composition may any of a number of types well known in the art, and does not require explanation in detail herein. Polymers known in the art to be useful in basecoat compositions include acrylics, vinyls, polyurethanes, polycarbonates, polyesters, alkyds, and polysiloxanes. Preferred polymers include acrylics and polyurethanes. In one preferred embodiment of the invention, the basecoat composition also utilizes a carbamate-functional acrylic polymer. Basecoat polymers may be thermoplastic, but are preferably crosslinkable and comprise one or more type of cross-linkable functional groups. Such groups include, for example, hydroxy, isocyanate, amine, epoxy, acrylate, vinyl, silane, and acetoacetate groups. These groups may be masked or blocked in such a way so that they are unblocked and available for the cross-linking reaction under the desired curing conditions, generally elevated temperatures. Useful cross-linkable functional groups include hydroxy, epoxy, acid, anhydride, silane, and acetoacetate groups. Preferred cross-linkable functional groups include hydroxy functional groups and amino functional groups.

Basecoat polymers may be thermoplastic, self-cross-linkable, or may require a separate cross-linking agent that is reactive with the functional groups of the polymer. When the polymer comprises hydroxy functional groups, for example, the cross-linking agent may be an aminoplast resin, isocyanate and blocked isocyanates (including isocyanurates), and acid or anhydride functional cross-linking agents.

Coating compositions of the invention can be coated on an article or surface by any of a number of techniques well known in the art. These include, for example, spray coating, dip coating, roll coating, curtain coating, and the like. For automotive body panels, spray coating is preferred.

The coating compositions described herein are preferably subjected to conditions so as to cure the coating layers. Although various methods of curing may be used, heat-curing is preferred. Generally, heat curing is effected by exposing the coated article to elevated temperatures provided primarily by radiative heat sources. Curing temperatures will vary depending on the particular blocking groups used in the cross-linking agents, however they generally range between 93° C. and 177° C. The compounds (C) according to the present invention are reactive even at relatively low cure temperatures. Thus, in a preferred embodiment, the cure temperature is preferably between 115° C. and 150° C., and more preferably at temperatures between 115° C. and 138° C. for a blocked acid catalyzed system. For an unblocked acid catalyzed system, the cure temperature is preferably between 82° C. and 99° C. The curing time will vary depending on the particular components used, and physical parameters such as the thickness of the layers, however, typical curing times range from 15 to 60 minutes, and preferably 15–25 minutes for blocked acid catalyzed systems and 10–20 minutes for unblocked acid catalyzed systems.

The invention is further described in the following examples. All parts and percentages are by weight unless otherwise specified.

EXAMPLES

Example 1

Preparation of the Monomeric Reactive Compound (2)

A mixture of 45.52 parts of 2-ethyl-1,3-hexanediol, 23.4 parts of methyl carbamate, 0.08 parts butyltin hydroxide oxide and 30.4 parts toluene was headed heated under an inert atmosphere to reflux in a reactor equipped with an extractor that can remove methanol but return toluene to the reaction mixture. Once at reflux, the inert atmosphere was turned off. The reaction was stopped when approximately half of the theoretical amount of mono-carbamate product was formed. Then 0.6 parts of octanethiol was added and the reaction mixture was held at 100° C. for 1.5 hours. Free methyl carbamate, toluene, octanethiol and some of the unconverted 2-ethyl-1,3-hexanediol was then removed by vacuum distillation. The final product was a mixture of 43.0% 2-ethyl-1,3-hexanediol and 53.2% 3-hydroxy-2-ethylhexane carbamate and 3.7% 2-ethyl-1,3-hexane dicarbamate.

Example 2a

Hypothetical Preparation of a Primary Carbamate Functional Ethylenically Unsaturated Monomer According to the Invention A mixture of 100 parts of 97% pure 3-chloro-2-ethylhexane carbamate and 100 parts of anhydrous butyl acetate is heated to 60° C. under a dried air atmosphere. Then 52 parts of sodium methacrylate and 0.04 parts of monomethyl ether hydroquinone are slowly added. The reaction is held at 60° C. until complete. The sodium chloride is removed by filtration followed by washings with water and brine solution. The butyl acetate is distilled off to produce 2-ethyl-3-methacrylate hexyl carbamate.

Example 2b

Hypothetical Preparation of a Primary Carbamate Functional Acrylic Polymer According to the Invention Thirty parts of amyl acetate is warmed up under an inert atmosphere to 140° C. Then a mixture of the 26 parts of the above acrylic monomer from Ex. 2a, 6.5 parts of cyclohexyl methacrylate, 13 parts of ethylhexyl acrylate, and 6.5 parts of methyl methacrylate and 4.5 parts of 2,2'-Dimethyl-2,2'-azodibutyronitrile are added over a four hour period. The reaction mixture is then held at 140° C. for one hour. The reaction mixture is then cooled to 110° C. and a mixture of 1 part of 2,2'-Dimethyl-2,2'-azodibutyronitrile in 10 parts of amyl acetate is added over 30 minutes. After the reaction mixture is held at 110° C. for 1 hour, the temperature is raised to 140° C. and held at 140° C. for 30 minutes. The final resin would have a NV of ~68% with a carbamate equivalent weight of ~670 g/equ on resin NV.

Example 3a

Hypothetical Preparation of a Primary Carbamate Functional Ethylenically Unsaturated Monomer According to the Invention A mixture of 100 parts of 3-hydroxy-2-ethylhexane carbamate and 100 parts of anhydrous amyl acetate is heated to 90° C. under a dried air atmosphere. Then 81.5 parts of methacrylic acid anhydride stabilized with 2000 ppm 2-Methyl-6-tert-butyl-p-cresol is slowly added. The reaction is followed by infrared spectrometry. The final product is an amyl acetate solution containing 16.2% methacrylic acid and 48.3% 2-ethyl-3-methacrylate hexyl carbamate.

Example 3b

Hypothetical Preparation of a Primary Carbamate Functional Acrylic Polymer According to the Invention Nine parts of amyl acetate and 25.6 parts of glycidyl neodecanoate is heated up under an inert atmosphere to 140° C. Then a mixture of 53.8 parts of the above solution from Ex 3a and 6.3 parts of 2,2'-Dimethyl-2,2'-azodibutyronitrile is added over four hours. Once the addition is complete, a mixture of 1 part of 2,2'-Dimethyl-2,2'-azodibutyronitrile and 4.3 parts of amyl acetate would be added over 15 minutes. The reaction mixture is held at 140° C. until the epoxy equivalent weight for the reaction mixture is less than 42,000 g/equ (on solution). The final product would have a NV of ~63.4% with a carbamate equivalent weight of ~627 g/equ and a hydroxy equivalent weight of ~627 g/equ.

Example 4a

Hypothetical Preparation of a Primary Carbamate Functional Ethylenically Unsaturated Monomer According to the Invention 100 parts of a mixture of 43.0% 2-ethyl-1,3-hexanediol from Ex 1 above and 53.2% 3-hydroxy-2-ethylhexane cartamate and 37% 2-ethyl-1,3-hexane dicarbamate in 100 parts of anhydrous butyl acetate is heated to 60° C. under a dried air atmosphere. Then 0.2 parts of dibutyl tin dilaurate are added. A mixture of 135 parts of 2-isocyanatoethyl methacrylate stabilized with 500 ppm 2,6-Di-tert-butyl-4-hydroxytoluene is slowly added. Once in, the reaction mixture is kept at 60° C. until the reaction is complete. Then 10 parts of methanol are added and the reaction mixture held at 60° C. for an additional hour. The butyl acetate is then carefully distilled off to produce a mixture of 57% 1.3-bis (isocyanatoethyl methacrylate urethane)-2-ethylhexane, 41% 2-ethyl-3-methacrylate hexyl carbamate and 2% 2-ethyl-1,3-hexane dicarbamate.

Example 4b

Hypothetical Preparation of a Primary Carbamate Functional Acrylic Polymer According to the Invention A mixture of 2.1 parts of DI water and 4.0 parts of ABEX EP-110 (From Rhodia Inc., Cranbury, N.J.) is heated to reflux under an inert atmosphere. The reaction mixture is then cooled to 82° C. and a mixture of 16.7 parts of DI water, 0.08 parts of ammonium persulfate, 1.7 parts of ABEX EP-110, 15.9 parts of butyl acrylate, 0.6 parts of 2-hydroxyethyl methacrylate, 2.0 parts of styrene is added over about 1 hour. Then 0.6 parts of DI water is added and the reaction mixture held for one hour at 82° C. Then two separate feeds are added simultaneously over one hour to the reaction mixture at 82° C. The first feed is made up of 12.1 parts of the above monomer mixture from Ex 4a and 0.5 parts of methacrylic acid. The second feed is made up of 5.0 parts of DI water and 0.02 parts of ammonium persulfate. Once these two additions are in, 9.9 parts of DI water is added and the reaction mixture held at 82° C. for two hours. The mixture is then cooled to below 40° C. and 9.8 parts of a 20% aminopropanol solution in DI water is added. The final resin will have a NV of ~41%

What is claimed is:

1. A primary carbamate functional acrylic polymer comprising randomly repeating units of the formula:

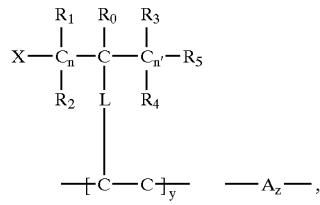

wherein x is a primary carbamate group, n is an integer of 2 or more, n' is an integer of 1 or more, $R_0$, $R_1$, $R_2$, $R_3$, $R_4$ and $R_5$ are independently H, an alkyl group, an aromatic group, or mixtures thereof, at least one $R_1$ or $R_2$ group is not hydrogen, L is a linking group, y represents from 2 to 100% by weight, based on the total weight of all ethylenically unsaturated monomers in the monomer mixture, A represents functional or nonfunctional repeating units derived from one or more ethylenically unsaturated monomers, z represents from 0 to 98% by weight, based on the total weight of all ethylenically unsaturated monomers in the monomer mixture, and substantially all primary carbamate groups x are attached to carbon atoms having a lower degree of substitution than a carbon atom to which linking group L is attached, wherein the primary carbamate functional acrylic polymer is the polymerization reaction product of a monomer mixture comprising a primary carbamate functional ethylenically unsaturated monomer of the structure:

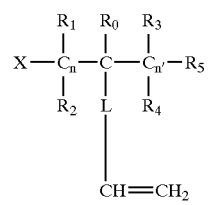

wherein X is a primary carbamate group, n is an integer of 2 or more, n' is an integer of 1 or more, $R_0, R_1, R_2, R_3, R_4$ and $R_5$ are independently H, an alkyl group, an aromatic group, or mixtures thereof, at least one $R_1$ or $R_2$ group is not hydrogen, and L is a linking group.

2. The primary carbamate functional acrylic polymer of claim 1 wherein the primary carbamate functional ethylenically unsaturated monomer comprises the reaction product of:

(1) an ethylenically saturated monomer comprising one or more functional groups (i) which are reactive with a functional group Z but which are substantially nonreactive with a primary carbamate group X of monomeric reactive compound (2), and (2) a monomeric reactive compound comprising one or more structures of the formula:

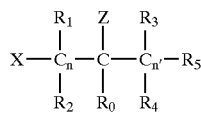

wherein

X is a primary carbamate group,

Z is a functional group reactive with at least one functional group of material (1) and is selected from the group consisting of hydroxy groups, halide groups, and derivatives thereof, n is an integer of 2 or more, n' is an integer of 1 or more, and $R_0, R_1, R_2, R_3, R_4$ and $R_5$ are independently H, an alkyl group, an aromatic group, or mixtures thereof, with the provisos that (i) at least one $R_1$ or $R_2$ group is not hydrogen, and (ii) in substantially all structures of monomeric reactive compound (2), primary carbamate group X is attached to a carbon atom having a lower degree of substitution than a carbon atom to which functional group Z is attached.

3. The primary carbamate functional acrylic polymer of claim 2 wherein linking group L is the reaction product of functional group (i) of the ethylenically unsaturated monomer and functional group Z of monomeric reactive compound (2).

4. The primary carbamate functional acrylic polymer of claim 3 wherein linking group L further comprises the reaction product of a reaction converting a hydroxy group into a derivative group of a hydroxy group.

5. The primary carbamate functional acrylic polymer of claim 3 wherein linking group L further comprises the reaction product of a reaction converting a halide group into a derivative group of a halide group.

6. The primary carbamate functional acrylic polymer of claim 3 wherein linking group L is selected from the group consisting of esters, ethers, urethanes, ureas, and silanes.

7. The primary carbamate functional acrylic polymer of claim 6 wherein linking group L is selected from the group consisting of esters and urethanes.

8. The primary carbamate functional acrylic polymer of claim 2 wherein Z is a functional derivative of a hydroxy group or a halide group.

9. The primary carbamate functional acrylic polymer of claim 8 wherein Z is a functional derivative of a hydroxy group or a halide group selected from the group consisting of acid groups, epoxy groups, cyclic carbonate groups, silane groups, isocyanate groups, amine groups especially primary and secondary amines, silicon hydrides, alkenes, organometallics, and mixtures thereof.

10. The primary carbamate functional acrylic polymer of claim 1 wherein y is from 40 to 100% by weight, based on the total weight of all ethylenically unsaturated monomers in the monomer mixture.

11. The primary carbamate functional acrylic polymer of claim 10 wherein y is from 80 to 100% by weight, based on the total weight of all ethylenically unsaturated monomers in the monomer mixture.

12. The primary carbamate functional acrylic polymer of claim 1 wherein z is from 0 to 60% by weight, based on the total weight of all ethylenically unsaturated monomers in the monomer mixture.

13. The primary carbamate functional acrylic polymer of claim 12 wherein z is from 0 to 20% by weight, based on the total weight of all ethylenically unsaturated monomers in the monomer mixture.

14. The primary carbamate functional acrylic polymer of claim 1 wherein z is from 0 to 20% by weight, based on the total weight of all ethylenically unsaturated monomers in the monomer mixture.

15. The primary carbamate functional acrylic polymer of claim 1 wherein A comprises repeating units resulting from the polymerization of nonfunctional ethylenically unsaturated monomers.

16. The primary carbamate functional acrylic polymer of claim 15 wherein A comprises repeating units resulting from the polymerization of nonfunctional ethylenically unsaturated monomers selected from the group consisting of alkyl vinyls, cycloaliphatic vinyls, aromatic vinyls, and mixtures thereof.

17. The primary carbamate functional acrylic polymer of claim 16 wherein A comprises repeating units resulting from the polymerization of nonfunctional ethylenically unsaturated monomers selected from the group consisting of methyl acrylate, methyl methacrylate, butyl methacrylate, cyclohexyl methacrylate, styrene, alpha-methyl styrene, and mixtures thereof.

18. The primary carbamate functional acrylic polymer of claim 1 wherein A comprises repeating units resulting from the polymerization of functional ethylenically unsaturated monomers.

19. The primary carbamate functional acrylic polymer of claim 18 wherein A comprises repeating units resulting from the polymerization of functional ethylenically unsaturated monomers selected from the group consisting of acid functional ethylenically unsaturated monomers, hydroxy-functional ethylenically unsaturated monomers, epoxy functional ethylenically unsaturated monomers, amino-functional ethylenically unsaturated monomers, lactone extended ethylenically unsaturated monomers, and mixtures thereof.

20. The primary carbamate functional acrylic polymer of claim 19 wherein A comprises repeating units resulting from the polymerization of functional ethylenically unsaturated monomers selected from the group consisting of acrylic acid, methacrylic acid, hydroxyethyl acrylate, hydroxybutyl acrylate, hydroxybutyl methacrylate, hydroxypropyl acrylate, glycidyl methacrylate, t-butylaminoethyl methacrylate, t-butylamino-ethylacrylate, and mixtures thereof.

21. The primary carbamate functional acrylic polymer of claim 1 wherein A comprises repeating units resulting from the polymerization of both functional and nonfunctional ethylenically unsaturated monomers.

22. The primary carbamate functional acrylic polymer of claim 1 wherein the ethylenically unsaturated monomer (1) further comprises one or more additional functional groups (ii) that are substantially nonreactive with primary carbamate group X but which are different from functional group (i).

23. The primary carbamate functional acrylic polymer of claim 2 wherein monomeric reactive compound (2) comprises one structure.

24. The primary carbamate functional acrylic polymer of claim 23 wherein monomeric reactive compound (2) comprises at least two structures.

25. The primary carbamate functional acrylic polymer of claim 2 wherein monomeric reactive compound (2) comprises at least four structures.

26. The primary carbamate functional acrylic polymer of claim 2 wherein Z is a hydroxy group.

27. The primary carbamate functional acrylic polymer of claim 1 wherein n is an integer of from 2 to 12.

28. The primary carbamate functional acrylic polymer of claim 27 wherein n is an integer of from 2 to 8.

29. The primary carbamate functional acrylic polymer of claim 28 wherein n is an integer of from 2 to 4.

30. The primary carbamate functional acrylic polymer of claim 1 wherein n is an integer of at least 3.

31. The primary carbamate functional acrylic polymer of claim 30 wherein n is an integer of from 3 to 12.

32. The primary carbamate functional acrylic polymer of claim 31 wherein n is an integer of from 3 to 4.

33. The primary carbamate functional acrylic polymer of claim 1 wherein n' is an integer of from 1 to 16.

34. The primary carbamate functional acrylic polymer of claim 33 wherein n' is 1 to 12.

35. The primary carbamate functional acrylic polymer of claim 34 wherein n' is 1 to 8.

36. The primary carbamate functional acrylic polymer of claim 1 wherein at least one of the substituents $R_1$ and $R_2$ on the carbon to which X is attached is hydrogen.

37. The primary carbamate functional acrylic polymer of claim 36 wherein both of the substituents $R_1$ and $R_2$ on the carbon to which X is attached are hydrogen.

38. The primary carbamate functional acrylic polymer of claim 37 wherein $R_0$ is H.

39. The primary carbamate functional acrylic polymer of claim 37 wherein $R_0$ is not hydrogen.

40. The primary carbamate functional acrylic polymer of claim 39 wherein $R_0$ is selected from the group consisting of $C_1$–$C_{16}$ aliphatic groups, $C_1$–$C_{16}$ cycloaliphatic groups, $C_1$–$C_{16}$ aromatic groups, and mixtures thereof.

41. The primary carbamate functional acrylic polymer of claim 40 wherein $R_0$ is selected from the group consisting of $C_1$–$C_{12}$ aliphatic groups.

42. The primary carbamate functional acrylic polymer of claim 41 wherein $R_0$ is selected from the group consisting of $C_1$–$C_8$ aliphatic groups.

43. The primary carbamate functional acrylic polymer of claim 36 wherein at least one of the substituents $R_1$ and $R_2$ on the carbon to which X is attached is not hydrogen and $R_0$ is not hydrogen.

44. The primary carbamate functional acrylic polymer of claim 43 wherein at least one of the $R_1$ or $R_2$ groups on the carbon to which X is attached is selected from the group consisting of $C_1$–$C_{16}$ aliphatic groups, $C_1$–$C_{16}$ cycloaliphatic groups, $C_1$–$C_{16}$ aromatic groups and mixtures thereof.

45. The primary carbamate functional acrylic polymer of claim 44 wherein $R_0$ is selected from the group consisting of $C_1$–$C_{16}$ aliphatic groups, $C_1$–$C_{16}$ cycloaliphatic groups, $C_1$–$C_{16}$ aromatic groups, and mixtures thereof.

46. The primary carbamate functional acrylic polymer of claim 45 wherein $R_0$ is selected from the group consisting of $C_1$–$C_{12}$ aliphatic groups.

47. The primary carbamate functional acrylic polymer of claim 46 wherein $R_0$ is selected from the group consisting of $C_1$–$C_8$ aliphatic groups.

48. The primary carbamate functional acrylic polymer of claim 1 wherein the at least one $R_1$ or $R_2$ group that is not hydrogen is attached to a carbon atom located in closer proximity to the carbon atom to which linking group L is attached than to the carbon atom to which primary carbamate group X is attached.

49. The primary carbamate functional acrylic polymer of claim 48 wherein n is 2 and the at least one $R_1$ or $R_2$ group that is not hydrogen is attached to a carbon atom located an equal distance between the carbon atom to which linking group L is attached and the carbon atom to which primary carbamate group X is attached.

50. The primary carbamate functional acrylic polymer of claim 48 wherein n is 3 or greater and the at least one $R_1$ or $R_2$ group that is not hydrogen is attached to a carbon atom located in closer proximity to the carbon atom to which functional group Y is attached than to the carbon atom to which functional group X is attached.

51. The primary carbamate functional acrylic polymer of claim 50 wherein n is 3 or greater and the at least one $R_1$ or $R_2$ group that is not hydrogen is attached to a carbon atom which is adjacent to the carbon atom to which functional group Y is attached.

52. The primary carbamate functional acrylic polymer of claim 1 wherein $R_3$, $R_4$ and $R_5$ are selected from the group consisting of H, $C_1$–$C_{16}$ aliphatic groups, $C_1$–$C_{16}$ cycloaliphatic groups, $C_1$–$C_{16}$ aromatic groups, and mixtures thereof.

53. The primary carbamate functional acrylic polymer of claim 1 wherein n' is greater than 1 and at least one of $R_3$, $R_4$ and $R_5$ are selected from the group consisting of $C_1$–$C_{16}$ aliphatic groups, $C_1$–$C_{16}$ cycloaliphatic groups, $C_1$–$C_{16}$ aromatic groups, and mixtures thereof.

54. The primary carbamate functional acrylic polymer of claim 53 wherein at least two of $R_3$, $R_4$ and $R_5$ are selected from the group consisting of $C_1$–$C_{16}$ aliphatic groups, $C_1$–$C_{16}$ cycloaliphatic groups, $C_1$–$C_{16}$ aromatic groups, and mixtures thereof.

55. The primary carbamate functional acrylic polymer of claim 54 wherein at least three of $R_3$, $R_4$ and $R_5$ are selected from the group consisting of $C_1$–$C_{16}$ aliphatic groups, $C_1$–$C_{16}$ cycloaliphatic groups, $C_1$–$C_{16}$ aromatic groups, and mixtures thereof.

56. The primary carbamate functional acrylic polymer of claim 2 wherein the monomeric reactive compound (2) consists of structures of the formula:

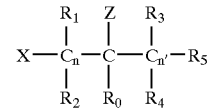

wherein

X is a primary carbamate group,

Z is a functional group reactive with at least one functional group of material (1) and is selected from the group consisting of hydroxy groups, halide groups, and derivatives thereof, n is an integer of 2 or more, n' is an integer of 1 or more, and $R_0$, $R_1$, $R_2$, $R_3$, $R_4$ and $R_5$ are independently H, an alkyl group, an aromatic group, or mixtures thereof, with the provisos that (i) at least one $R_1$ or $R_2$ group is not hydrogen, and (ii) primary carbamate group X is attached to a carbon atom having a lower degree of substitution than a carbon atom to which functional group Z is attached.

57. A method of making a primary carbamate functional acrylic polymer, comprising polymerizing a monomer mixture comprising a primary carbamate functional ethylenically unsaturated monomer of the structure:

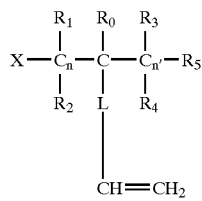

wherein X is a primary carbamate group, n is an integer of 2 or more, n' is an integer of 1 or more, $R_0$, $R_1$, $R_2$, $R_3$, $R_4$ and $R_5$ are independently H, an alkyl group, an aromatic group, or mixtures thereof, at least one $R_1$ or $R_2$ group is not hydrogen, L is a linking group, and said primary carbamate functional ethylenically unsaturated monomer comprises the reaction product of (1) an ethylenically saturated monomer comprising one or more functional groups (i) which are reactive with a functional group Z but which are substantially nonreactive with a primary carbamate group X of monomeric reactive compound (2), and (2) a monomeric reactive compound comprising one or more structures of the formula:

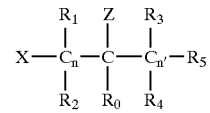

wherein

X is a primary carbamate group,

Z is a functional group reactive with at least one functional group of material (1) and is selected from the group consisting of hydroxy groups, halide groups, and derivatives thereof, n is an integer of 2 or more, n' is an integer of 1 or more, and $R_0$, $R_1$, $R_2$, $R_3$, $R_4$ and $R_5$ are independently H, an alkyl group, an aromatic group, or mixtures thereof, with the provisos that (i) at least one $R_1$ or $R_2$ group is not hydrogen, and (ii) in substantially all structures of monomeric reactive compound (2), primary carbamate group X is attached to a carbon atom having a lower degree of substitution than a carbon atom to which functional group Z is attached.

58. A curable coating composition comprising the primary carbamate functional acrylic polymer of claim 1.

* * * * *